(12) United States Patent
Okamoto et al.

(10) Patent No.: US 6,960,432 B2
(45) Date of Patent: Nov. 1, 2005

(54) DETECTION/QUANTIFICATION OF TARGETED NUCLEOTIDE CHAINS, AND DETECTION/QUANTIFICATION OF MULTI-STRANDED NUCLEOTIDE CHAINS BY FLUORESCENCE

(75) Inventors: Tadashi Okamoto, Yokohama (JP); Nobuko Yamamoto, Isehara (JP); Tomohiro Suzuki, Sagamihara (JP)

(73) Assignee: Canon Kabushiki Kaisha, Tokyo (JP)

( * ) Notice: Subject to any disclaimer, the term of this patent is extended or adjusted under 35 U.S.C. 154(b) by 297 days.

(21) Appl. No.: 09/764,050

(22) Filed: Jan. 19, 2001

(65) Prior Publication Data

US 2002/0068282 A1 Jun. 6, 2002

(51) Int. Cl.[7] .............................. C12Q 1/68; C12P 19/34; C07H 21/02; C07H 21/04
(52) U.S. Cl. .......................... 435/6; 435/91.2; 435/395; 536/23.1; 536/24.3; 536/25.32
(58) Field of Search ........................... 435/6, 91.2, 395; 536/23.1, 24.3, 25.32

(56) References Cited

U.S. PATENT DOCUMENTS

| | | | |
|---|---|---|---|
| 5,624,798 A | 4/1997 | Yamamoto et al. ............. | 435/6 |
| 5,670,315 A | 9/1997 | Yamamoto et al. ............. | 435/6 |
| 5,939,256 A | 8/1999 | Yamamoto et al. ............. | 435/6 |
| 6,156,506 A | 12/2000 | Yamamoto et al. ............. | 435/6 |
| 6,268,131 B1 * | 7/2001 | Kang et al. ..................... | 435/6 |
| 6,277,628 B1 * | 8/2001 | Johann et al. ............ | 435/287.2 |

FOREIGN PATENT DOCUMENTS

| | | | |
|---|---|---|---|
| JP | 03095862 | * 4/1991 | |
| WO | 87/06956 | * 11/1987 | |
| WO | WO 93/15221 | 8/1993 | ............ C12Q/1/44 |

OTHER PUBLICATIONS

Yamamoto, et al.; "A Rapid Detection of PCR Amplification Product Using a New Fluorescent Intercalator; The Pyrylium Dye, P2"; 23 8 (1995), 1445–1446.
Lecture Resumes II (665) for the 72nd spring meeting of the Chemistry Society Of Japan (1997).

* cited by examiner

Primary Examiner—Kenneth R. Horlick
Assistant Examiner—Joyce Tung
(74) Attorney, Agent, or Firm—Fitzpatrick, Cella, Harper and Scinto

(57) ABSTRACT

A method for dry detection/quantification of targeted nucleotide chains, comprising the steps of:

(1) realizing a state in which a hybrid (C) of a certain amount of targeted nucleotide chain (A), which is derived from a sample solution and subjected to detection or quantification, and a probe nucleotide chain (B), which has a base sequence complementary to a specific site of the base sequence of the targeted nucleotide chain, is formed on a solid-phase substrate by mutually reacting the two types of nucleotide chains with each other, and in which there exists a fluorescence dye (D), which acts on the hybrid (C), thereby emits fluorescence or increases its fluorescence intensity, and is capable of continuing to emit fluorescence even in the dried state while acting on the hybrid;

(2) drying the hybrid (C) and the fluorescence dye (D) on the substrate; and (3) measuring the fluorescence emitted from the fluorescence dye (D), as a measuring means, after the drying operation.

26 Claims, 12 Drawing Sheets

DETECTION/QUANTIFICATION OF MODEL TARGETED NUCLEOTIDE CHAIN BY HYBRID NUCLEOTIDE CHAIN SOLUTION METHOD (DRY METHOD)

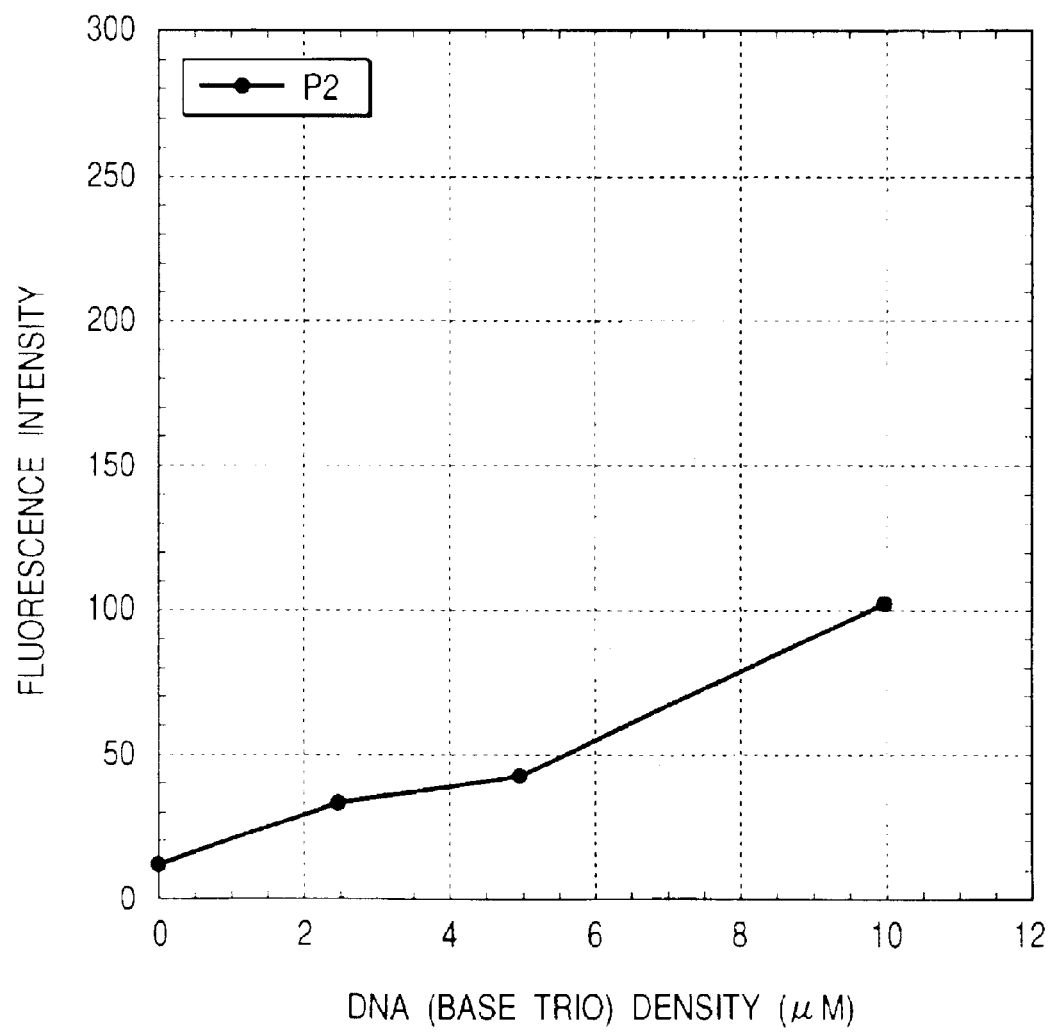

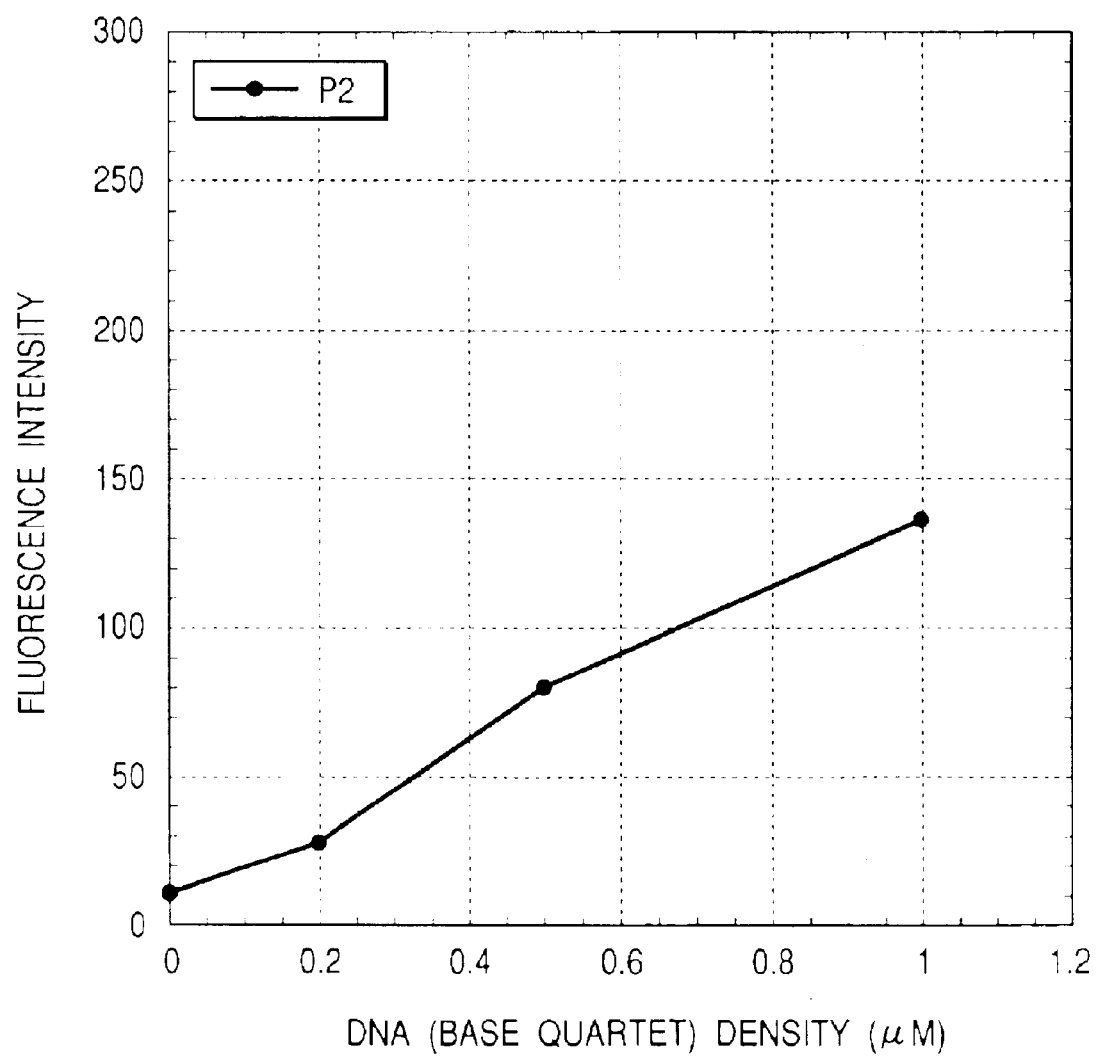

DETECTION/QUANTIFICATION OF TARGETED NUCLEOTIDE CHAINS, AND DETECTION/QUANTIFICATION OF MULTI-STRANDED NUCLEOTIDE CHAINS BY FLUORESCENCE

BACKGROUND OF THE INVENTION

1. Field of the Invention

The present invention relates to detection/quantification of targeted nucleotide chains with specific base sequences therein and detection/quantification of multi-stranded nucleotide chains such as double-stranded nucleotide chains.

2. Related Background Art

In order to detect specific genes of organisms, in the detection of a double-stranded nucleotide hybrid of a targeted nucleotide chain and a nucleotide probe for the targeted nucleotide chain, a technology has been widely used of detecting/quantifying the double-stranded nucleotide chain in gel or solution using fluorescence dyes, such as ethidium bromide (hereinafter referred to as EB), which act on double-stranded nucleotide chains and increase their fluorescence intensity.

In recent years, while polymerase chain reaction, which replicates nucleotide chains with an enzyme, has been very commonly used to detect a very slight amount of nucleotide chains, a method has also been used which uses 2-methyl-4,6-bis(4-N,N-dimethylaminophenyl)pyrylium salt, a dye emitting fluorescence only after acting on double-stranded nucleotide chains in solution, to detect the PCR amplification products (Nucleic Acid Research, 1995, Vol. 23, No. 8 1445–1446).

Further, quite recently, a fact has been known that there exist in organisms triple-stranded and quadruple-stranded nucleotide chains having special base sequences and those nucleotide chains play an important part in the replication of genes and the lifetime of cells in organisms.

These nucleotide chains form triple-stranded chains and quadruple-stranded chains and, in each chain, 3 or 4 bases in corresponding positions form a base trio or a base quartet in a plane.

Although there have been very few studies on dyes acting on these triple- and quadruple-stranded chains, in particular on fluorescence dyes, there is found in a collection of lecture resumes II (665) for the 72th spring meeting of the Chemistry Society of Japan (1997) a description that 2-methyl-4,6-bis(4-N,N-dimethylaminophenyl)pyrylium salt acts on triple- and quadruple-stranded DNAs and emit fluorescence in a solution.

Further, besides of the above dye, there have been several dyes, including YOYO1 from Molecular Probe Co., on the market in recent years.

Among these dyes, EB is generally considered to be an intercalator which enters the space between the two base pairs of double-stranded nucleotide chains, and there is found in a literature (Nucleic Acid Symposium Series No. 29 1993 83–84) a description that 2-methyl-4,6-bis(4-N,N-dimethylaminophenyl)pyrylium salt is also an intercalator. On the other hand, YOYO1 is generally considered to be a groove binding type fluorescence dye which enters the groove of double-stranded nucleotide chains.

The method, what is called solid-phase hybridization, is widely known which forms a hybrid on a solid phase by fixing a targeted nucleotide chain, which has a specific base sequence, for use in detection of a specific gene or fixing a probe nucleotide chain having a base sequence complementary to a specific site of the base sequence of the targeted nucleotide chain on a solid phase and by reacting the same with the corresponding probe nucleotide chain or targeted nucleotide chain to detect the hybrid thereof. And there have been developed various detecting techniques.

The most typical technique is the Southern hybridization technique, which forms a hybrid on, for example, a nylon filter by transferring a nucleotide chain, which is developed according to their length utilizing gel electrophoresis, to the nylon filter, denaturing the same to be single-stranded, and allowing a probe nucleotide chain labeled with a radioisotope to act on the same, so as to detect the formed hybrid thereof by using autoradiography.

And in order to overcome the problems attendant to the use of radioisotope, an improved technique has been put to practical use which uses chemiluminescence as a detecting means.

In recent years, as means for detecting a specific gene more simply and easily, a technique has also been developed which forms a hybrid on a micro-plate by fixing a probe nucleotide chain on the micro-plate and allowing a mRNA targeted nucleotide chain to act on the same, so as to detect the formed hybrid thereof with a dye, for example, ethidium bromide (hereinafter referred to as EB), which acts specifically on double-stranded nucleotide chains and thereby increase its fluorescence intensity (published Japanese Laid-Open Application of PCT Patent Application No. 7-506482).

As described above, there have been known dyes which act on double-stranded nucleotide chains or multi-stranded nucleotide chains in solution and thereby increase their fluorescence intensity or emit fluorescence for the first time; however, what is known about them is just the behavior in solution.

Usually for the determination of the fluorescence characteristics (intensity, excitation/fluorescence spectrum, etc.) of fluorescence dyes, measurements are made for about 1 to 4 mL of sample solution with a dye dissolved therein placed in measuring glass cells, generally with a spectrofluorometer. Micro-cells of about 200 $\mu$L are also commercially available. And, lately, devices are also commercially available from several manufacturers which make measurements automatically and continuously for sample solutions placed in about 100 to 250 $\mu$L wells up to 96 of a plastic micro-plate (for example, Cyto Flour, by Nippon Perceptive Ltd.).

In any of these measurements, since measurements are made for the sample solution in solution as described above, the containers for use in the measurements are restricted, further, when making measurements using a micro-plate, if the sample is illuminated with excitation light from the solution surface side, there occurs a problem of causing diffused reflection and scattering on the solution surface, and the illumination has to be conducted from the plate back side.

Further, when the amount of the sample solution is as small as 0.5 to 5 $\mu$L, the containers for use in the measurements are limited. In addition, when trying to measure fluorescence with a microscope, there arise not only a problem of excitation direction as described above, but also a problem of permitting the sample to be dried and the fluorescence of the same to be quenched, even in a typical fluorescence dye, FITC (fluorescein isothiocyanate).

SUMMARY OF THE INVENTION

In light of the above problems, the present inventors concentrated their energies on an intensive investigation of the detection/quantification of targeted nucleotide chains, in particular, of multi-stranded nucleotide chains including double-stranded nucleotide chains, and have finally made the present invention.

According to one aspect of the present invention, there is provided a method for dry detection/quantification of targeted nucleotide chains comprising the steps of:

(1) realizing a state in which a hybrid (C) of a certain amount of targeted nucleotide chain (A), which is derived from a sample solution and subjected to detection or quantification, and a probe nucleotide chain (B), which has a base sequence complementary to a specific site of the base sequences of the targeted nucleotide chain, is formed on a solid-phase substrate by mutually reacting the above two types of nucleotide chains with each other, and in which there exists a fluorescence dye (D), which acts on the hybrid (C), thereby emits fluorescence or increases its fluorescence intensity, and is capable of continuing to emit fluorescence even in the dried state while acting on the hybrid;

(2) drying the hybrid (C) and the fluorescence dye (D) on the substrate; and (3) measuring the fluorescence emitted from the fluorescence dye (D), as a measuring means, after the drying operation.

According to another aspect of the present invention, there is provided a method for detection/quantification of multi-stranded nucleotide chains comprising the steps of:

(1) adding to a sample solution, which is subjected to detection/quantification of a multi-stranded nucleotide chain, a fluorescence dye having a fluorescence characteristic of emitting fluorescence or increasing its fluorescence intensity in the presence of a multi-stranded nucleotide chain and capable of maintaining the fluorescence characteristic even in the dried state;

(2) placing a known amount of the sample solution with the fluorescence dye added thereto on a clean observation substrate so as to dry the same; and (3) measuring the fluorescence emitted from the dried sample and detecting/quantifying the multi-stranded nucleotide chain in the sample solution based on the obtained measured values.

The present invention enables the observation of targeted nucleotide chains by fluorescence even under dry conditions. This brings the following good results: the restrictions on the containers used for detection/quantification of targeted nucleotide chains can be relaxed; even a very slight amount of sample can be used without caring about its getting dried; the detecting/quantifying operations become relatively simpler and easier because of dry conditions; and the direction in which excitation light is illuminated is not restricted.

Further, in an aspect in which a hybrid of a targeted nucleotide chain and a probe nucleotide chain is fixed on a substrate at the final stage, nucleotide chains other than the hybrid or the fluorescence dye used can be removed by washing operation, as the need arises. This reduces the background, resulting in higher detection/quantification sensitivity.

BRIEF DESCRIPTION OF THE DRAWINGS

FIG. 11 is a graphical representation of detection/quantification of a triple-stranded nucleotide chain using P2; and FIG. 12 is a graphical representation of detection/quantification of a quadruple-stranded nucleotide chain using P2.

DETAILED DESCRIPTION OF THE PREFERRED EMBODIMENTS

Figure 1:
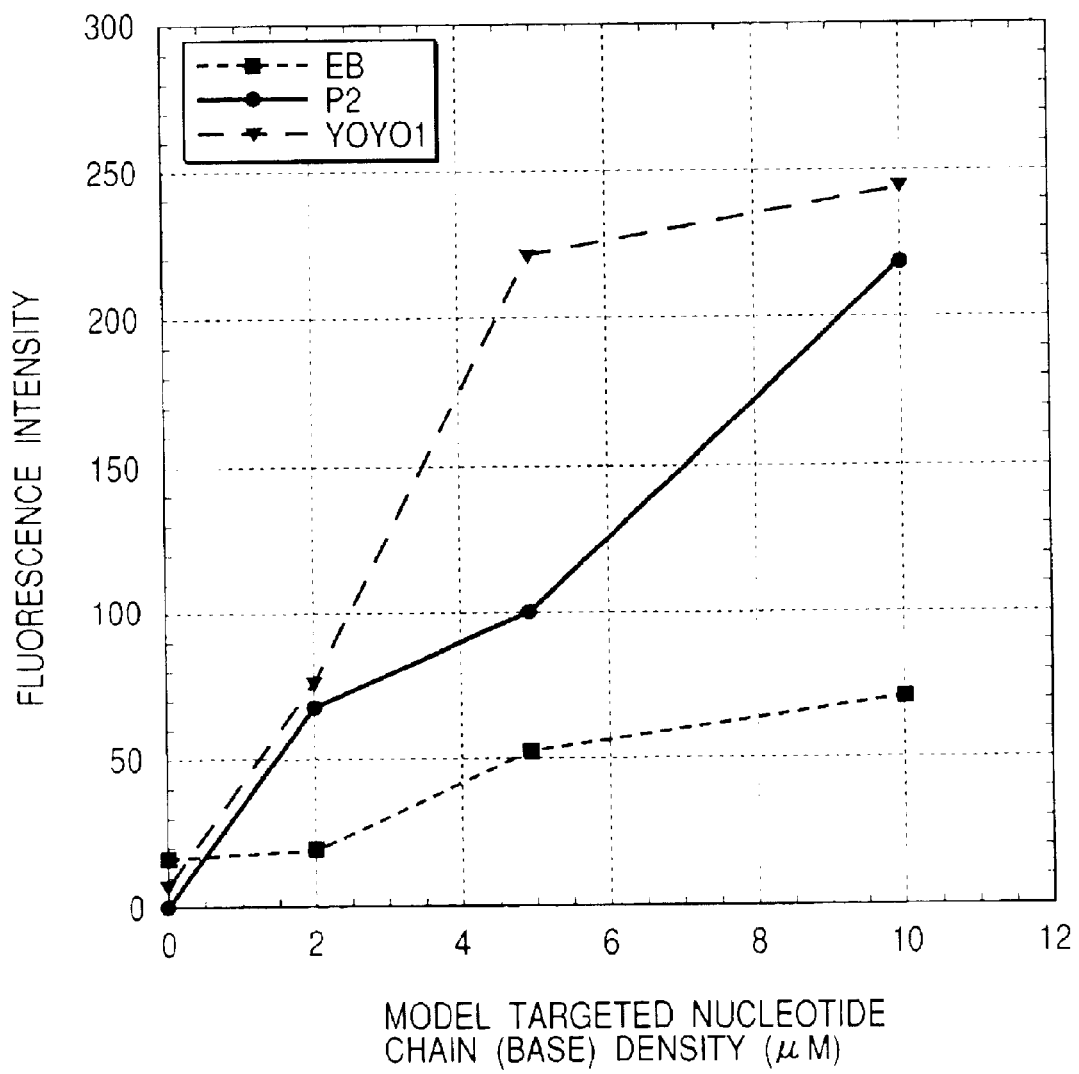
FIG. 1 is a graphical representation of detection/quantification of a model targeted nucleotide chain using EB, P2 and YOYO1 by the hybrid nucleotide chain solution method (solution system)

The method for detection/quantification of targeted nucleotide chains of the present invention is dry detection/quantification of targeted nucleotide chains characterized in that they comprise:

a step (1) of realizing a state in which a hybrid (C) of a certain amount of targeted nucleotide chain (A), which is derived from a sample solution and subjected to detection or quantification, and a probe nucleotide chain (B), which has a base sequence complementary to a specific site of the base sequence of the targeted nucleotide chain, is formed on a solid-phase substrate by mutually reacting the above two types of nucleotide chains with each other, and in which there exists a fluorescence dye (D), which acts on the hybrid (C), thereby emits fluorescence or increases its fluorescence intensity, and is capable of continuing to emit fluorescence even in the dried state while acting on the hybrid;

a step (2) of drying the hybrid (C) and the fluorescence dye (D) on the substrate; and a step (3) of measuring the fluorescence emitted from the fluorescence dye (D), as a measuring means, after the drying operation.

In the above step (1), the formation (1-1) of the hybrid (C) and the action (1-2) of the fluorescence dye (D) on the hybrid (C) may be carried out:

(a) in state where they are dissolved in the sample solution; or (b) in state where they are fixed on the substrate.

The latter (b) case includes a step (1-0) or (1-0') of previously fixing either one of the targeted nucleotide chain (B) or the probe nucleotide chain (A) on the clean observation solid-phase substrate, and after this step, the formation (1-1) of the hybrid (C) is carried out by allowing the other solution to act on the fixed solid, subsequently the action (1-2) of the fluorescence dye (D) on the hybrid (C) is carried out.

At this time, as the need arises, the following washing steps may be added:

a step (1-1') of removing the nucleotide chain other than the hybrid (C) in the solution by washing operation after the formation (1-1) of the hybrid (C) and before the action (1-2) of the fluorescence dye (D) on the hybrid (C);

a step (1-3) of removing the fluorescence dye (D) not having acted on the hybrid (C) after the action (1-2) of the fluorescence dye (D) on the hybrid (C); and a step (1-4) of removing the solvent including the hybrid (C) and the fluorescence dye (D) having acted on the hybrid (C) by gas flow between the above steps (1) and (2).

In the (b) case, though there are different cases where the probe nucleotide chain (B) is fixed on the solid-phase substrate and the targeted nucleotide chain (A) is fixed on the same, there is basically no difference in means for detecting the hybrid (C) of the targeted nucleotide chains and the probe nucleotide chains finally formed on the solid-phase substrate surface.

According to the present invention, the hybrid (C) of the targeted nucleotide chain and the probe nucleotide chain as well as the fluorescence dye (D) having acted on the above hybrid finally exist on the substrate surface in the form of a dried thin film with a certain area; therefore, handling the sample becomes easier, and the direction of excitation light illumination is not restricted because there exists no liquid. In addition, the restrictions on the sample container used are relaxed substantially, since the fluorescence is measured for the sample in the dried state.

It goes without saying that if the amount of each solution used before the step (2) is relatively large, the container is needed which has concave portions corresponding to the amount; however, if the amount of the same is sufficiently small, a planar substrate may be used.

However, in the case of (a), when quantitative evaluation is required, it becomes necessary to prepare micro concave portions with which the area of the dropped liquid can be specified.

Further, according to the present invention, the step is not necessary, in principle, of removing the fluorescence dye (D) not having acted on the hybrid by washing operation, because the dye (D) used for acting on the targeted nucleotide chains in the solution is such that it emits fluorescence or increases its fluorescence intensity only after acting on the hybrid (C) of the targeted nucleotide chains and the probe nucleotide chains.

However, in the case of (b), because the hybrid (C) to be detected at the final stage is fixed on the surface of the solid-phase substrate, particularly when using the fluorescence dye of a type which increases its fluorescence intensity after acting on the hybrid, it becomes easier to remove the dye not having acted on the hybrid by washing operation so as to reduce the background, as the need arises, and it also becomes easier to remove the nucleotide chains other than the hybrid formed on the solid-phase substrate by washing operation so as to reduce the background.

Further, according to the present invention, the problem of the fluorescence being quenched by drying the sample solution can be avoided in principle, because the fluorescence dye (D) is used which is capable of continuing to emit fluorescence even in the dried state while acting on the double-stranded nucleotide chains and the hybrid.

Any fluorescence dyes may be used in the present invention as long as they emit fluorescence or increase their fluorescence intensity only after acting on the hybrid in a solution and are capable of continuing to emit fluorescence even in the dried state while acting on the hybrid.

The mechanism is not clear for the fluorescence dye used in the present invention to act on the nucleotide chain hybrid and continue to emit fluorescence even in the dried state; however, considering the fact that in the sole solutions of either of FITC and rhodamine, which have high fluorescence intensity (from another viewpoint, high quantum yield of fluorescence) and are relatively stable in a solution, their fluorescence is rapidly quenched once they are left in the dried state, it is presumed that the micro-environment of the fluorescence dye in the present invention undergoes some change when the dye acts on the nucleotide chain and becomes suitable for the fluorescence emission.

From that viewpoint, the modes in which the fluorescence dye in the present invention acts on the nucleotide chain hybrid are desirably such that its dye molecules are included in the nucleotide chain hybrid.

The fluorescence dye's action modes described above include, for example, intercalation in which the dye molecules enter the space between the two base pairs of the nucleotide chain hybrid, which is a double-stranded nucleotide chain, and groove binding in which the dye molecules enter the groove of the double-stranded nucleotide chain.

After the intensive investigation of the fluorescence intensity and safety of the dyes acting on the nucleotide chain hybrid in these modes, the present inventors have found that EB and 2-methyl-4,6-bis(4-N,N-dimethylaminophenyl) pyrylium salt are desirable as intercalators and YOYO1 is desirable as a groove binding type dye. It goes without saying that these dyes are not intended to limit the present invention.

Any nucleotide chains may be the targeted nucleotide chains detectable/quantifiable by the present invention as long as they hybridize with probe nucleotide chains. Both DNA and RNA can be the targeted nucleotide chains of the present invention.

However, in the case of (a), if there exist in the solution double-stranded nucleotide chains other than the hybrid of the targeted nucleotide chains and the probe nucleotide chains, the double-stranded nucleotide chains other than the hybrid are also detected in principle; thus, the double-stranded nucleotide chains other than the hybrid need to be discriminated and removed. In order to remove such operations, nucleotide chains previously separated into single strands or RNA which is single-stranded from the beginning are desirably used as the targeted nucleotides.

Further, among RNAs, mRNA, of which partially double-stranded portion is small compared with tRNA and rRNA, is more desirably used as the targeted nucleotide chains.

On the other hand, in the case of the method (b), since the nucleotide chains other than the hybrid can be easily removed by washing operation, as described above, both single-stranded and double-stranded nucleotide chains can be subjected to detection as they are by controlling hybridization conditions. In terms of the capability of making the detection easier, single-stranded nucleotide chains may be more desirably used as the targeted nucleotide chains; however, there is basically no difference between the two types nucleotide chains. Among single-stranded nucleotide chains, mRNA, which has small partially double-stranded portion and codes directly the amino acid sequence, is more desirably used, just like the case of (a).

In the method (b) of the present invention, as the substrate on which a hybrid of a targeted nucleotide chain and a probe nucleotide chain is finally fixed, any substrates may be used as long as the hybrid can be attached thereto. The substrates include, for example, glass substrates formed of synthetic quartz, fused quartz or others and resin substrates formed of acryl, polycarbonate, polystyrene or others.

In the use of the above substrates, according to the method of the present invention, the restrictions are relaxed which are imposed on the excitation light illumination direction when detecting fluorescence; however, when using, for example, a fluorescence microscope which illuminates the substrate, on which the substances to be detected are fixed, with excitation light from its back side, the substrate is required to be optically transparent to the wavelength of both excitation light and fluorescence emitted.

On the other hand, even when using a fluorescence microscope which illuminates the substrate with excitation light from its substance side, in view of the scattering of excitation light, the substrate is desirably optically transparent like the above case or desirably such that it can control the reflection of excitation light to some extent, like a black mirror finished or black frosted substrate. Translucent substrates are not desirable, especially in view of the scattering of excitation light.

As the method of attaching the targeted nucleotide chain or probe nucleotide chain used in the present invention on a substrate, any methods may be adopted as long as they allow the targeted nucleotide chain or probe nucleotide chain to attach on the substrate, allow the same to form a hybrid with the probe nucleotide chain or targeted nucleotide chain, and allow the hybrid to be detected/quantified by the method of the present invention.

In such a case, the nylon filters used in the aforementioned Southern hybridization or the like can also be used in principle; however, in view of the efficiency in hybridization or the aforementioned fluorescence detecting method, desirably a method is adopted to bond targeted nucleotide chain or probe nucleotide chain covalently on a substrate which is advantageous to optical detection.

In recent years, as substrates for use in such a method, polystyrene micro-plates with amino group attached thereon (brand name: Sumiron N) and with carboxyl group attached thereon (brand name: Sumiron C) are commercially available from Sumitomo Bakelite Co., Ltd.

The nucleotide chain can be attached on the substrate by the method which activates the above amino group and the hydroxyl group at 5' terminal of the nucleotide chain with carbonyldiimidazole so as to subject the same to peptide bond, or by the method which subject the above carboxyl group and the nucleotide chain with primary amino group attached thereto to attachment by the method described in published Japanese Laid-Open Application of PCT Patent Application No. 7-506482. Alternatively, the method can also be adopted which introduces a maleimide group to the above carboxyl group, followed by subjecting the carboxyl group and the nucleotide chain with sulfhydryl group attached thereto to attachment.

In addition, the method can also be adopted which applies an aminosilane coupling agent on a glass substrate, followed by subjecting the amino group and the nucleotide chain to attachment in the same manner as described above, or which applies a glycidylsilane coupling agent on a glass substrate, followed by subjecting the epoxy group and the amino group attached to the nucleotide chain or amino group of the nucleotide chain base to attachment in such a manner as not to interfere with hybridization.

The substrate have only to be in the dried state which enables the elimination of the obstacles to fluorescence measurements due to the existence of water having a flow property or due to its containing moisture. The dry conditions under which water does not interfere with fluorescence measurements should be determined, for example, based on the data obtained by preparing a sample equivalent to that of the actual measurements, conducting a pretest in accordance with the same sample drying procedure as an actual one, and making NMR measurements for the dried sample.

The concrete drying methods include, for example, the drying-up method using a vacuum pump as adopted in the following examples; however, the methods are not limited to such an example and any methods can be adopted as long as they have the effect equivalent to that of the drying-up method.

The detection/quantification of multi-stranded nucleotide chains of the present invention are characterized in that they comprise the steps of:

(1) adding to a sample solution, which is subjected to detection/quantification of multi-stranded nucleotide chains, a fluorescence dye having a fluorescence characteristic of emitting fluorescence or increasing its fluorescence intensity in the presence of the multi-stranded nucleotide chains and capable of maintaining the fluorescence characteristic even in the dried state;

(2) placing a known amount of the sample solution with the fluorescence dye added thereto on a clean observation substrate so as to dry the same; and (3) measuring the fluorescence emitted from the dried sample and detecting/quantifying the multi-stranded nucleotide chains in the sample solution based on the obtained measured values.

According to the present invention, multi-stranded nucleotide chains as well as the fluorescence dye having acted on the above multi-stranded nucleotide chains exist on the substrate surface in the form of a dried thin film with a certain area at the final stage; therefore, handling the sample becomes easier, and the direction of excitation light illumination is not restricted. In addition, the restrictions on the sample container used are relaxed substantially, since the fluorescence is measured for the sample in the dried state.

It goes without saying that if the amount of the solution dropped in the step (2) is relatively large, the container is needed which has concave portions corresponding to the amount; however, if the amount of the same is sufficiently small, a planar substrate may be used. However, when quantitative evaluation is required, it becomes necessary to prepare micro concave portions with which the area of the dropped liquid can be specified.

Further, according to the present invention, the step is not necessary, in principle, of removing the fluorescence dye not having acted on the multi-stranded nucleotide chains by washing operation, because the dye used for acting on the multi-stranded nucleotide chains in the solution is such that it emits fluorescence or increases its fluorescence intensity only after acting on the multi-stranded nucleotide chains. In addition, the problem of the fluorescence's being quenched by drying the sample solution, as described above, can be avoided in principle, because the fluorescence dye is used which is capable of continuing to emit fluorescence even in the dried state while acting on the multi-stranded nucleotide chains.

Any fluorescence dye may be used in the present invention as long as it emits fluorescence or increases its fluorescence intensity only after acting on the multi-stranded nucleotide chains in the solution and is capable of continuing to emit fluorescence even in the dried state while acting on the multi-stranded nucleotide chains.

The mechanism is not clear for the fluorescence dye used in the present invention to act on the multi-stranded nucleotide chains and continue to emit fluorescence even in the dried state; however, considering the fact that in the sole solutions of either of FITC and rhodamine, which have high fluorescence intensity (from another viewpoint, high quantum yield of fluorescence) and are relatively stable in a solution, their fluorescence is rapidly quenched once they are left in the dried state, it is presumed that the microenvironment of the fluorescence dye in the present invention undergoes some change when the dye acts on the multi-stranded nucleotide chain and becomes suitable for the fluorescence emission.

From that viewpoint, the modes in which the fluorescence dye in the present invention acts on the multi-stranded nucleotide chain are desirably such that its dye molecules are included in the multi-stranded nucleotide chain. The fluorescence dye's action modes described above include, for example, intercalation in which the dye molecules enter the space between the two base pairs of the multi-stranded nucleotide chains including double-stranded nucleotide chains, and groove binding in which the dye molecules enter the groove of the multi-stranded nucleotide chain.

After the intensive investigation of the fluorescence intensity and safety of the dyes acting on the multi-stranded nucleotide chains in these modes, the present inventors have found that EB and 2-methyl-4,6-bis(4-N,N-dimethylaminophenyl)pyrylium salt are desirably used as intercalators and YOYO1 is desirably used as a groove binding type dye in the dry detection/quantification of multi-stranded nucleotide chains by fluorescence.

It goes without saying that these dyes are not intended to limit the present invention.

The multi-stranded nucleotide chains detectable/quantifiable by the present invention may include not only the ordinary double-stranded DNA, but also the triple-stranded DNA and quadruple-stranded DNA as described above, in addition, natural type multi-stranded nucleotide chains such as DNA-RNA hybrid and RNA-RNA hybrid, multi-stranded nucleotide chains of which backbone has a non-natural type structure, such as those at least one strand of which is phosphorothionate-type or hydrogenphosphonate-type or protein nucleotide chains of which backbone consists of nucleotide, and non-natural type nucleotide chains of which saccharified portion or base portion is modified. And any nucleotide chains may be included as long as they are capable of forming multi-stranded chains by recognizing their partners with hydrogen bond between bases.

The substrate have only to be in the dried state which enables the elimination of the obstacles to fluorescence measurements due to the existence of water having a flow property or due to its containing moisture. The dry conditions under which water does not interfere with fluorescence measurements should be determined, for example, based on the data obtained by preparing a sample equivalent to that of the actual measurements, conducting a pretest in accordance with the same sample drying procedure as an actual one, and making NMR measurements for the dried sample.

The concrete drying methods include, for example, the drying-up method using a vacuum pump as adopted in the following examples; however, the methods are not limited to such an example and any methods can be adopted as long as they have the effect equivalent to that of the drying-up method.

In the following, the present invention will be described in detail with reference to the following examples.

EXAMPLE 1

Detection of Oligodeoxynucleotide with EB, 2-Methyl-4,6-bis(4-N,N-Dimethylaminophenyl)Pyrylium Iodide (hereinafter referred to as P2) and YOYO1

(1) 20-mer oligodeoxynucleotide having completely the same base sequence as the specific part of that of M13mp18, which is a single-stranded DNA, was obtained (from Kanto Chemical Co., Ltd.) as a model targeted nucleotide chain. The base sequence was as follows:
5'ACTGGCCGTCGTTTTACAAC3'
(SEQ ID NO: 1)
A 100 $\mu$M, in terms of the base concentration, stock solution of the model targeted nucleotide chain was prepared by properly mixing the aqueous solution of the above oligonucleotide and water.

(2) 20-mer oligodeoxynucleotide having base sequence complementary to that of the above model targeted nucleotide chain was obtained as a probe nucleotide chain, and a 100 $\mu$M, in terms of the base concentration, stock solution of the probe nucleotide chain was prepared in the same manner as described in (1). The base sequence was as follows:
3'TGACCGGCAGCAAAATGTTG5'
(SEQ ID NO: 2)

(3) Four mg of EB (from Sigma Ardrich Japan) was dissolved in 1 mL of DMSO and 9 mL of water was added. Additional water was added to the solution to bring about a 100-fold dilution as a 10 $\mu$M stock solution.

(4) Five mg of P2 (synthesized by the present inventors) was dissolved in 1 mL of acetonitrile and 9 mL of water was added. Additional water was added to the solution to bring about a 100-fold dilution as a 10 $\mu$M stock solution.

(5) Water was added to YOYO1 (from Molecular Probe Co., 1 mM/DMSO) to bring about a 100-fold dilution as a 10 $\mu$M stock solution.

(6) Each of 0, 2, 5, 10 $\mu$L of model targeted nucleotide chain solutions (final concentrations of 0, 2.0, 5.0 and 10.0 $\mu$M, respectively, at the stage where a dye solution has been added), 15 $\mu$L of probe nucleotide chain solution (a final concentration of 15 $\mu$M) and 5 $\mu$L of 100 mM Tris-HCl buffer solution (pH 7.5) were mixed and water was added to a volume of 90 $\mu$L. Each solution was annealed and cooled to a final temperature of 4° C.

(7) Ten $\mu$L (final concentration 1 $\mu$M) of each dye solution was added to each of the above DNA solutions.

(8) 0.5 $\mu$L of each solution (5) was placed on a properly cleaned and dried transparent acrylic substrate 1 mm thick (from Asahi Chemical Industry Co., Ltd., Deluglass A). For the solutions in the above state and another solutions having been subjected to the same operation as above and the drying-up by a vacuum pump, the fluorescence was observed and the intensity of the same was measured.

For the fluorescence observation, used was an inverted-type fluorescence microscope IMT2 (objective lens of 10 magnifications) from Olympus Optical Co., Ltd. And as the filter cubes for the fluorescence observation, a G excitation filter was used for each case using EB, a B excitation filter for each case using YOYO1 and a filter specially prepared (by Asahi Bunko, excitation: 580 nm, fluorescence: 540 nm, dichroic mirror: 610 nm) for each case using P2.

For the measurements of fluorescence intensity, used were a CCD equipped with an image intensifier (from Hamamatsu Photonics, ICCD C2400-87) and an image processing apparatus (from Hamamatsu Photonics, Argus 50) which were connected to the above fluorescence microscope via a relay lens (NFK 2.5×LD).

The measurements of fluorescence intensity were carried out in the area of 200×200 μm which was considered to have the average brightness and be uniform to some extent, and the average values on the pixels (2×2 μm) in the area were adopted as measured values.

The amplification degree of the image intensifier was 0.2 in terms of the indicated value. The fluorescence intensity values of the dyes cannot be directly compared because the spectral characteristics of the filters are different from each other, the excitation light source (high pressure mercury lamp) consists of bright lines, and because the sensitivity of the ICCD camera depends on wavelength.

Figure 2:
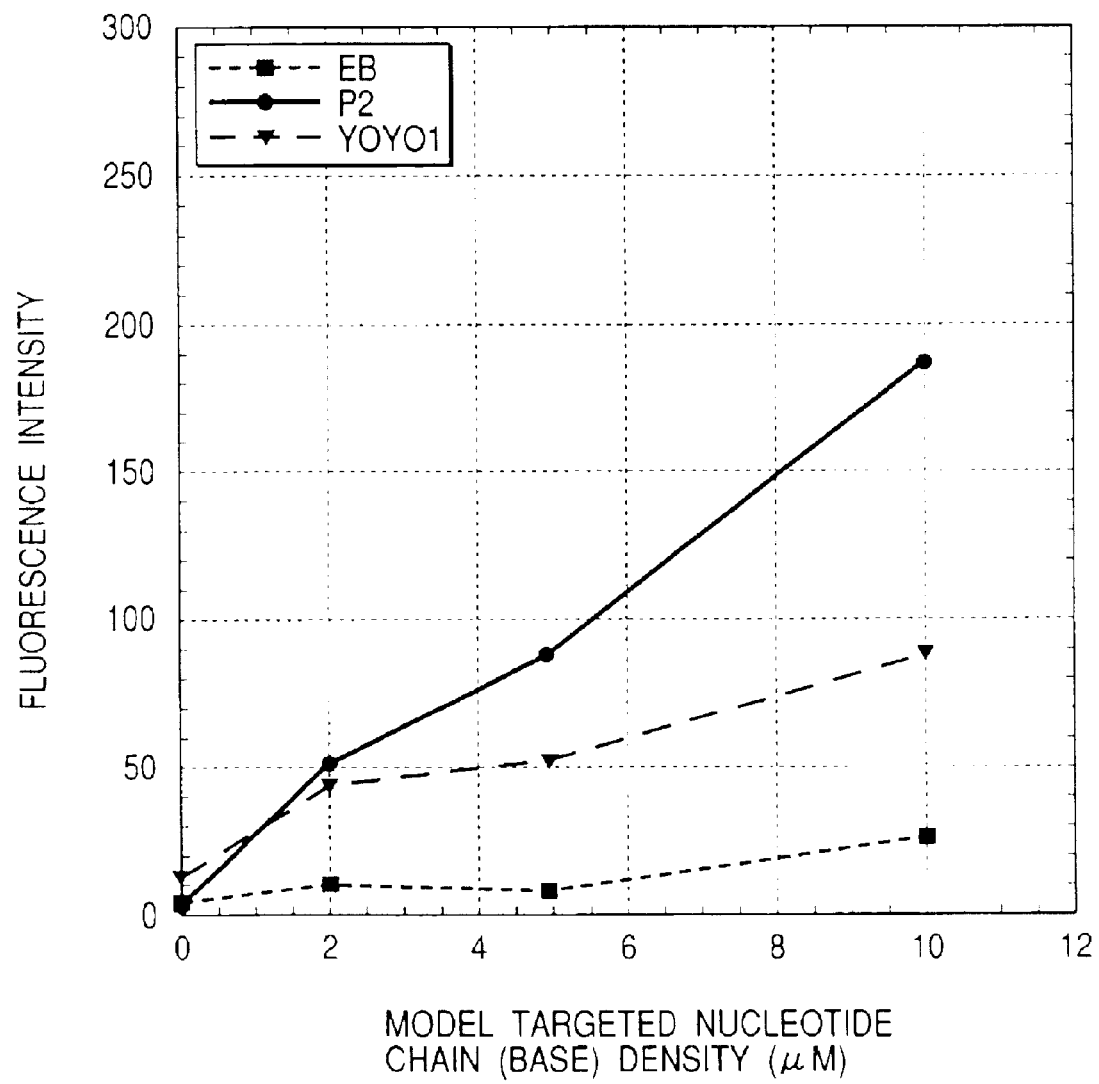
FIG. 2 is a graphical representation of detection/quantification of a model targeted nucleotide chain using EB, P2 and YOYO1 by the hybrid nucleotide chain solution method (dry method)

The measured values of the fluorescence intensity are shown in FIGS. 1 (solution system) and 2 (dry type). It is apparent from FIGS. 1 and 2 that the detection/quantification of model targeted nucleotide chains can be performed even in the dry-up state with any one of EB, P2 and YOYO1, though there are observed differences in fluorescence intensity difference and linearity. The comparison of the three types of dyes shows that the degree of fluorescence quenching is high in EB and YOYO1, especially in EB, in the dried up state. On the other hand, the degree of fluorescence quenching is relatively low in P2 in the dried up state; accordingly, P2 can be said to be suitable for the measuring method of the present invention.

EXAMPLE 2

Detection of Targeted DNA with EB, P2 and YOYO1

(1) M13mp18 (from Takara Shuzo Co., Ltd.), which is a single-stranded DNA, was obtained as a targeted nucleotide chain. The targeted base sequence was the same as in Example 1, as shown below:
5'ACTGGCCGTCGTTTTACAAC3'
(SEQ ID NO: 1)

A 10 μM, in terms of the base concentration of the targeted portion, a stock solution of the targeted nucleotide chain was prepared by properly mixing the aqueous solution of the above DNA and water. The reason that the concentration of the base of the targeted portion was dilute compared with that of Example 1 is that, since M13mp18 consists of 7249 bases, the concentration as a nucleotide chain had to be kept properly.

(2) Ten μM aqueous solution of oligodeoxynucleotide having the same base sequence as in Example 1, as shown below, was prepared as a probe nucleotide chain stock solution.
3'TGACCGGCAGCAAAATGTTG5'
(SEQ ID NO: 2)

(3) Ten μM stock solutions of EB, P2 and YOYO1 were prepared in the same manner as in Example 1.

(4) Each of 0, 2, 5, 10 μL of targeted nucleotide chain solutions (final concentrations of 0, 0.2, 0.5 and 1.0 μM, respectively, at the stage where a dye solution has been added), 15 μL of probe nucleotide chain solution (a final concentration of 1.5 μM) and 5 μL of 100 mM Tris-HCl buffer solution (pH 7.5) were mixed and water was added to a volume of 99 μL. Each solution was annealed and cooled to a final temperature of 4° C.

(5) 1.0 μL (final concentration 0.1 μM) of each dye solution was added to each of the above DNA solutions.

(6) The fluorescence intensity of the sample was measured in the same manner as in Example 1 in state where the sample was dried up.

The amplification degree of the image intensifier was 1.0 in terms of the indicated value, because the concentration of the targeted DNA was low.

Figure 3:
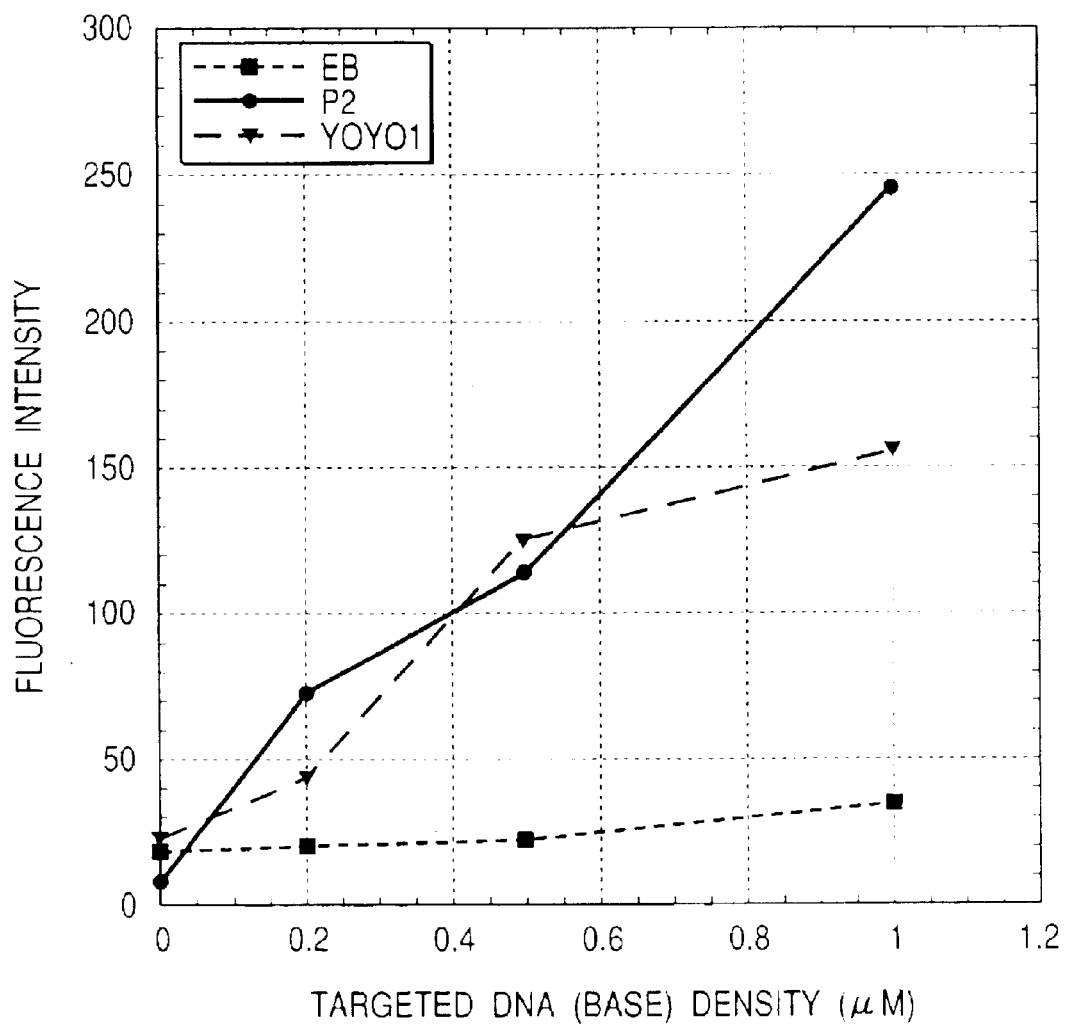
FIG. 3 is a graphical representation of detection/quantification of M13mp18 using EB, P2 and YOYO1 by the hybrid nucleotide chain solution method.

The measured results are shown in FIG. 3. It is apparent from FIG. 3 that the targeted single-stranded nucleotide chains can be detected/quantified by the method of the present invention.

EXAMPLE 3

Detection of Targeted mRNA with P2

(1) Human $\beta_2$ adrenergic receptor mRNA was synthesized from human $\beta_2$ adrenergic receptor cDNA using $T_7$RNA polymerase by conventional procedure and purified after the D Nase treatment. A 10 μm, in terms of the base concentration of the targeted portion, stock solution of a targeted nucleotide chain was prepared by properly mixing the aqueous solution of the above mRNA and water.

The portion of the targeted base sequence of the above mRNA was as follows:
5'TGCTGTGCGTCACGGCCAGCAT3'
(SEQ ID NO: 3)

(2) Ten μM aqueous solution of oligodeoxynucleotide (from Kanto Chemical Co., Ltd.) having the following base sequence was prepared as a probe nucleotide chain stock solution.
3'ACGACACGCAGTGCCGGTCGTA5'
(SEQ ID NO: 4)

(3) Ten μM stock solution of P2 was prepared in the same manner as in Example 1.

(4) Each of 0, 2, 5, 10 μL of targeted nucleotide chain solutions (final concentrations of 0, 0.2, 0.5 and 1.0 μM, respectively, at the stage where a dye solution has been added), 15 μL of probe nucleotide chain solution (a final concentration of 1.5 μM) and 5 μL of 100 mM Tris-HCl buffer solution (pH 7.5) were mixed and water was added to a volume of 90 μL. And the solution was annealed and cooled to a final temperature of 4° C.

(5) 1.0 μL (final concentration 0.1 μM) of P2 solution was added to each of the above DNA solutions.

(6) The fluorescence intensity of the sample was measured in the same manner as in Example 2 in state where the sample was dried up.

Figure 4:
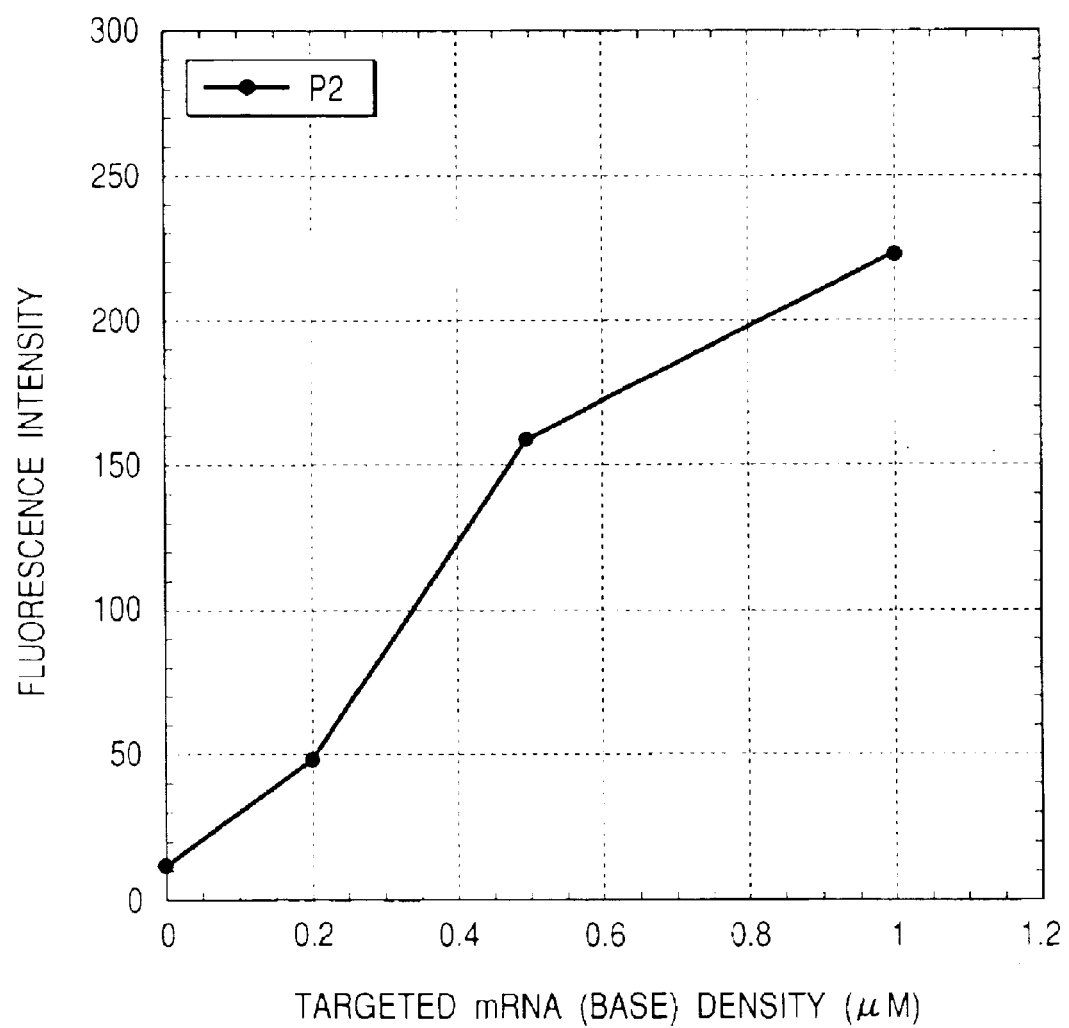
FIG. 4 is a graphical representation of detection/quantification of mRNA using P2 by the hybrid nucleotide chain solution method.

The measured results are shown in FIG. 4. It is apparent from FIG. 4 that the targeted mRNA can be detected/quantified by the method of the present invention.

EXAMPLE 4

Detection of Oligodeoxynucleotide with EB, 2-methyl-4, 6-bis(4-N,N-dimethylaminophenyl)pyrylium iodide (hereinafter referred to as P2) and YOYO1 (probe nucleotide chain being fixed)

(1) The same 20-mer oligodeoxynucleotide (from Kanto Chemical Co., Ltd.) as used in Example 1 was used as a model targeted nucleotide chain. The base sequence was as follows:
5'ACTGGCCGTCGTTTTACAAC3'
(SEQ ID NO: 1)

A 100 μM, in terms of the base concentration, stock solution of the model targeted nucleotide chain was prepared by properly mixing the aqueous solution of the above oligonucleotide and water.

(2) 20-mer oligodeoxynucleotide having base sequence complementary to that of the above model targeted nucleotide chain was obtained as a probe nucleotide chain, and a 100 μm, in terms of the base concentration, stock solution of the probe nucleotide chain was prepared in the same manner as described in (1). In order to fix the probe nucleotide chain on a solid-phase substrate by the covalent bond, 20-mer oligodeoxynucleotide was obtained and used at which 5' terminal an amino group was attached using hexamethylene as a linker. The base sequence was as follows:
3'TGACCGGCAGCAAAATGTTG-NH$_2$5'
(SEQ ID NO. 2)

(3) Ten μM stock solutions of EB, P2 and YOYO1 were prepared in the same manner as in Example 1.

(4) The probe nucleotide chain of (2) was fixed on a 96-well micro-plate with carboxyl groups attached to its surface (from Sumitomo Bakelite Co., Ltd., Sumiron C) using 1-hyroxy-2,5-dioxo-3-pyrrolidinesulfonic acid monosodium salt (from Sigma Ardrich Japan, hereinafter referred to as sulfoNHS) and 1-ethyl-3-(3 dimethylaminopropyl) carbodiimide hydrochloride (from Sigma Ardrich Japan, hereinafter referred to as EDC) in accordance with the method disclosed in the published Japanese Laid-Open Application of PCT Patent Application.

(5) Each of 0, 2, 5, 10 μL of the model targeted nucleotide chain solutions (final concentrations of 0, 2.0, 5.0 and 10.0 μM, respectively) and 5 μL of 100 mM Tris-HCl buffer solution (pH 7.5) were mixed in the wells of the above micro-plate and water was added to 100 μL. And the solution were annealed and cooled to a final temperature of 4° C. Each of the following steps before fluorescence observation was carried out at 4° C.

(6) Since it was considered that the targeted nucleotide chain was used in excess of the probe nucleotide chain attached on the well surface of the micro-plate, the wells were emptied and washed with 100 μL of the above buffer solution three times, and 90 μL of the above buffer solution was added.

(7) Ten μL (final concentration of 1 μM) of each dye solution was added to the above DNA solution and left stand for about 10 minutes, then each dye solution was removed by suction.

(8) The wells were washed with 100 μL of the above buffer solution once, and this solution was removed by suction.

(9) The micro-plate was dried up with a vacuum pump, and the fluorescence was observed and the intensity of the same was measured. In addition to this, fluorescence was measured for the solution system to which 100 μL of 10 mM Tris-HCl buffer solution (pH 7.5) was added after the step (10).

The amplification degree of the image intensifier was 4.0 in terms of the indicated value.

Figure 5:
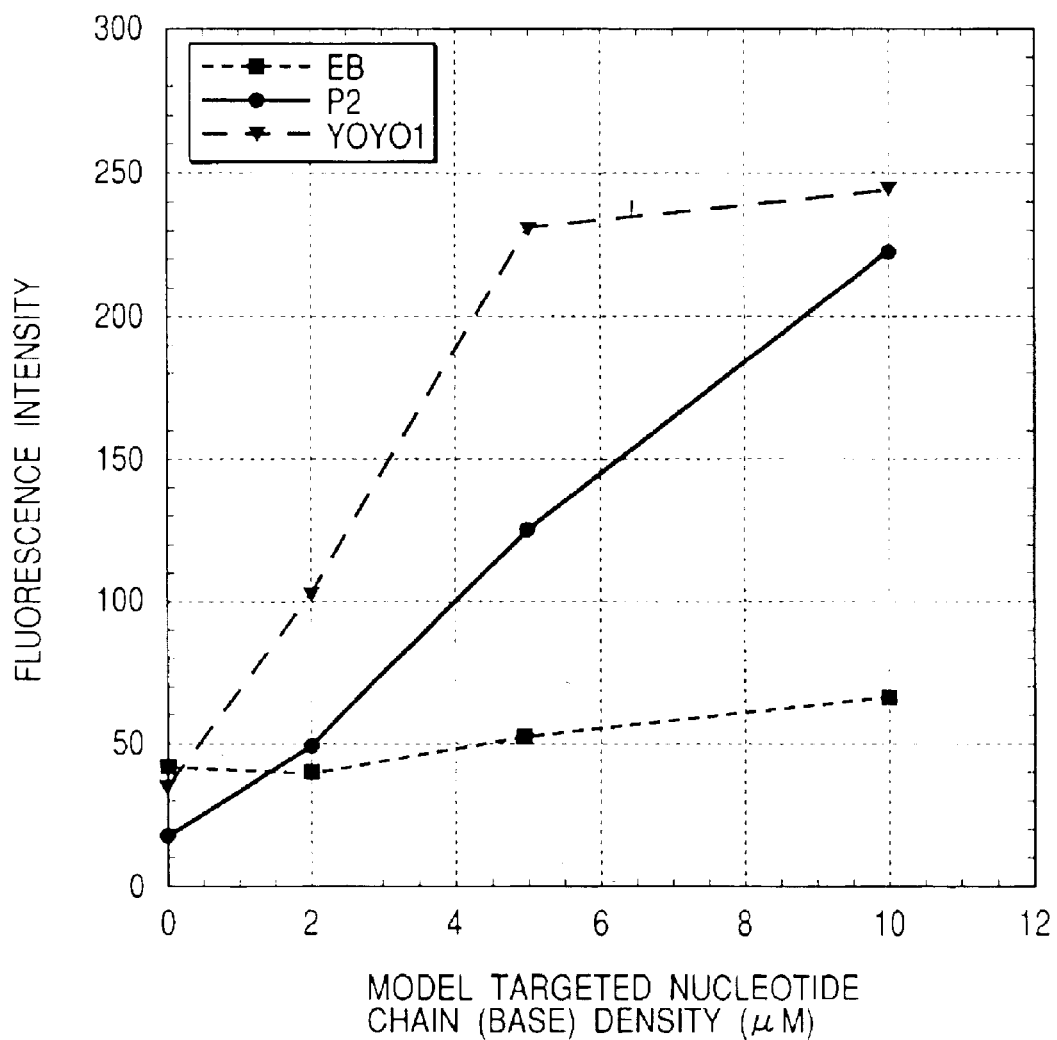
FIG. 5 is a graphical representation of detection/quantification of a model targeted nucleotide chain using EB, P2 and YOYO1 by the probe nucleotide chain fixing method (solution system)
Figure 6:
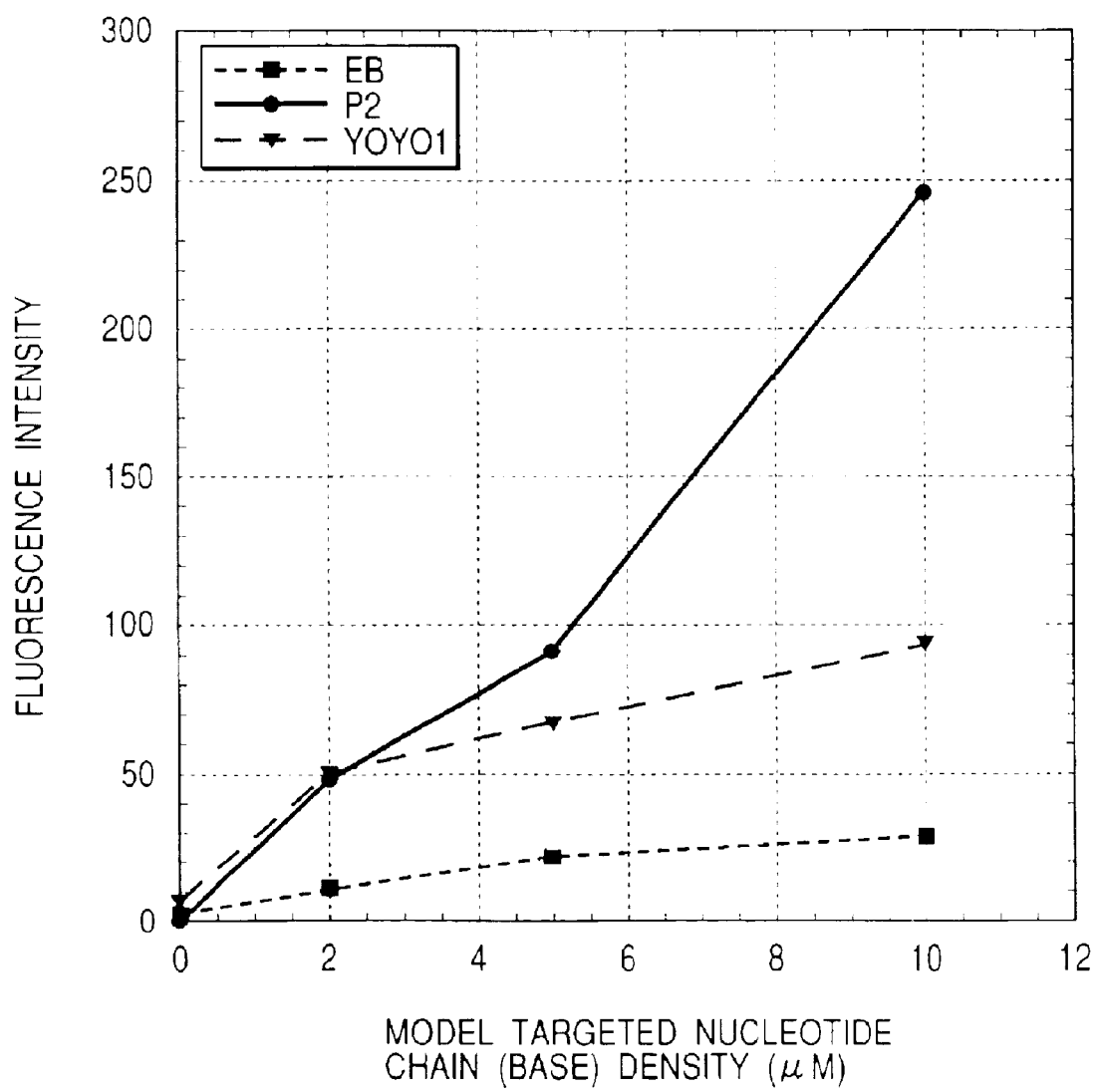
FIG. 6 is a graphical representation of detection/quantification of a model targeted nucleotide chain using EB, P2 and YOYO1 by the probe nucleotide chain fixing method (dry method)

The measured values of the fluorescence intensity are shown in FIGS. 5 (solution system) and 6 (dry type). It is apparent from FIGS. 5 and 6 that the detection/quantification of model targeted nucleotide chains can be performed even in the dry-up state with any one of EB, P2 and YOYO1, though there are observed differences in fluorescence intensity difference and linearity. The comparison of the three types of dyes shows that the degree of fluorescence quenching is high in EB and YOYO1, especially in EB, in the dried up state. On the other hand, the degree of fluorescence quenching is relatively low in P2 in the dried up state; accordingly, P2 can be said to be suitable for the measuring method of the present invention.

EXAMPLE 5

Detection of Targeted DNA with P2 (probe nucleotide chain being fixed)

(1) M13mp18 (from Takara Shuzo Co., Ltd.), the same single-stranded DNA as used in Example 2, was used as a targeted nucleotide chain. The targeted base sequence was the same as in Examples 1 and 4, as shown below:
5'ACTGGCCGTCGTTTTACAAC3'
(SEQ ID NO: 1)

A 10 μM, in terms of the base concentration of the targeted portion, stock solution of the targeted nucleotide chain was prepared by properly mixing the aqueous solution of the above DNA and water. The reason that the concentration of the base of the targeted portion was dilute compared with that of Example 5 is that, since M13mp18 consists of 7249 bases, the concentration as a nucleotide chain had to be kept properly.

(2) 20-mer oligodeoxynucleotide having base sequence complementary to that of the above model targeted nucleotide chain was obtained as a probe nucleotide chain in the same manner as in Example 4, and a 100 μm, in terms of the base concentration, stock solution of the probe nucleotide chain was prepared in the same manner as described in (1). The base sequence was as follows:
3'TGACCGGCAGCAAAATGTTG-NH$_2$5'
(SEQ ID NO. 2)

(3) The probe nucleotide chain of (2) was fixed on a micro-plate in the same manner as in Example 4.

(4) Each of 0, 2, 5, 10 μL of the targeted nucleotide chain solutions (1) (final concentrations of 0, 0.2, 0.5 and 1.0 μM, respectively) and 5 μL of 100 mM Tris-HCl buffer solution (pH 7.5) were mixed in the wells of the above micro-plate and water was added to 100 μL. And the solutions were annealed and cooled to a final temperature of 4° C. Each of the following steps before fluorescence observation was carried out at 4° C.

(5) The wells were emptied and washed with 100 μL of the above buffer solution three times, and 90 μL of the above buffer solution was added.

(6) Ten μL (final concentration of 1 μM) of P2 solution prepared in the same manner as in Example 4 was added to the above DNA solution and left stand for about 10 minutes, then the dye solution was removed by suction.

(7) The wells were washed with 100 μL of the above buffer solution once, and this solution was removed by suction.

(8) The fluorescence intensity was measured in state the sample was dried up in the same manner as in Example 4.

Figure 7:
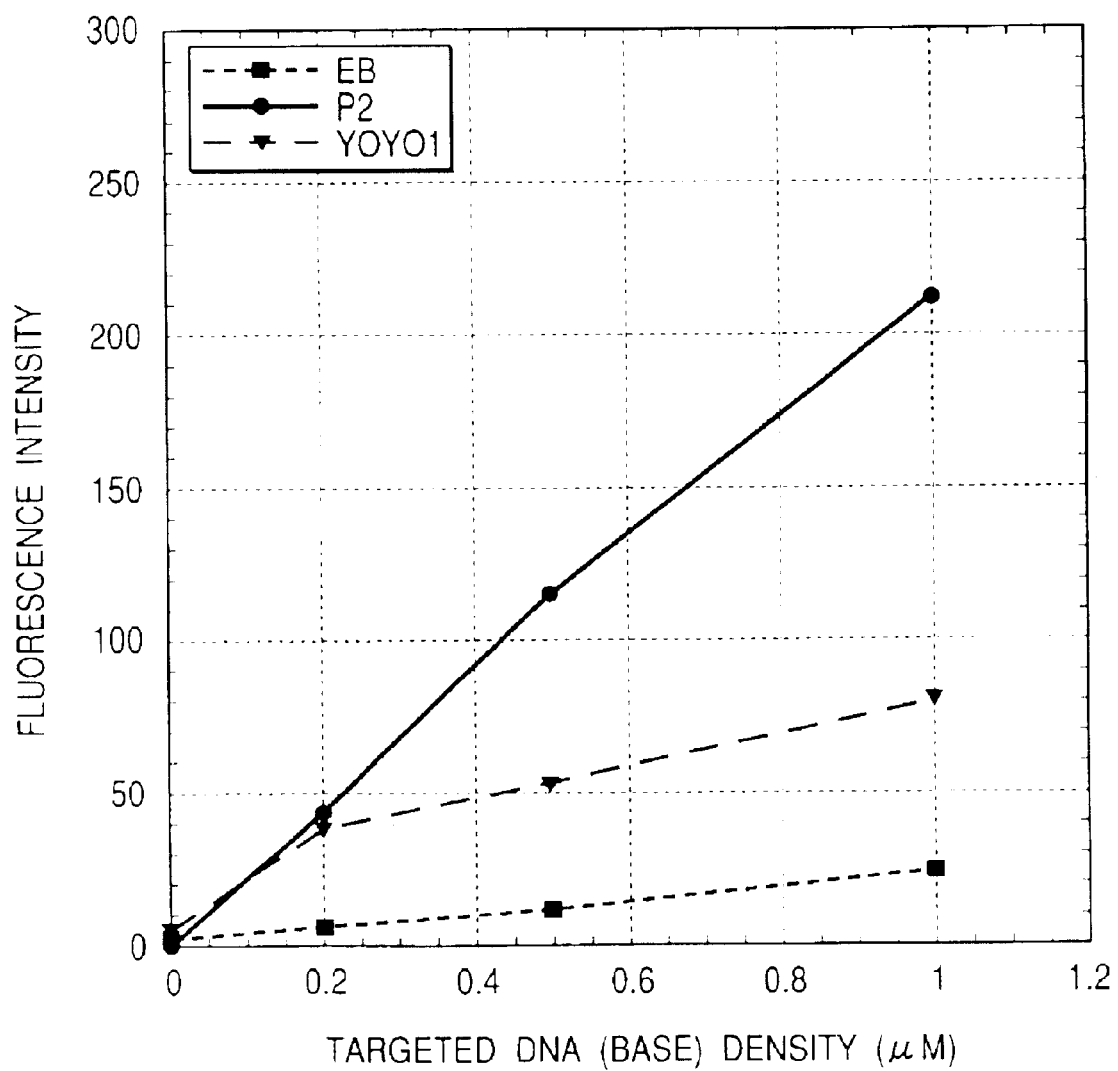
FIG. 7 is a graphical representation of detection/quantification of M13mp18 using EB, P2 and YOYO1 by the probe nucleotide chain fixing method.

The measured values of the fluorescence intensity are shown in FIG. 7. It is apparent from FIG. 7 that the targeted single-stranded DNA can be detected/quantified by the method of the present invention.

EXAMPLE 6

Detection of Targeted mRNA with P2 (probe nucleotide chain being fixed)

(1) Human β$_2$ adrenergic receptor mRNA was synthesized from human β$_2$ adrenergic receptor cDNA using T$_7$RNA polymerase by conventional procedure and purified after the D Nase treatment. A 10 μm stock solution of targeted nucleotide chain was prepared as a base of the targeted portion by properly mixing the aqueous solution of the above mRNA and water.

The portion of the targeted base sequence of the above mRNA was as follows:
5'TGCTGTGCGTCACGGCCAGCAT3'
(SEQ ID NO: 3)

(2) Ten μM aqueous solution of oligodeoxynucleotide (from Kanto Chemical Co., Ltd.) having the following base sequence was prepared as a probe nucleotide chain stock solution. An amino group was attached at the 5' terminal of this oligodeoxynucleotide like Examples 4 and 5.

3'ACGACACGCAGTGCCGGTCGTA-NH₂5
(SEQ ID NO: 4)

(3) The probe nucleotide chain of (2) was fixed on a micro-plate in the same manner as in Example 4.

(4) Each of 0, 2, 5, 10 μL of targeted mRNA solutions (final concentrations of 0, 0.2, 0.5 and 1.0 μM, respectively) and 5 μL of 100 mM Tris-HCl buffer solution (pH 7.5) were mixed in the wells of the above micro-plate and water was added to a volume of 100 μL. And the solution was annealed and cooled to a final temperature of 4° C. Each of the following steps before fluorescence observation was carried out at 4° C.

(5) The wells were emptied and washed with 100 μL of the above buffer solution three times, and 90 μL of the above buffer solution was added.

(6) Ten μL (final concentration of 1 μM) of P2 solution prepared in the same manner as in Example 4 was added to the above solution and left stand for about 10 minutes, then the dye solution was removed by suction.

(7) The wells were washed with 100 μL of the above buffer solution once, and this solution was removed by suction.

(8) The fluorescence intensity was measured in state the sample was dried up in the same manner as in Example 4.

Figure 8:
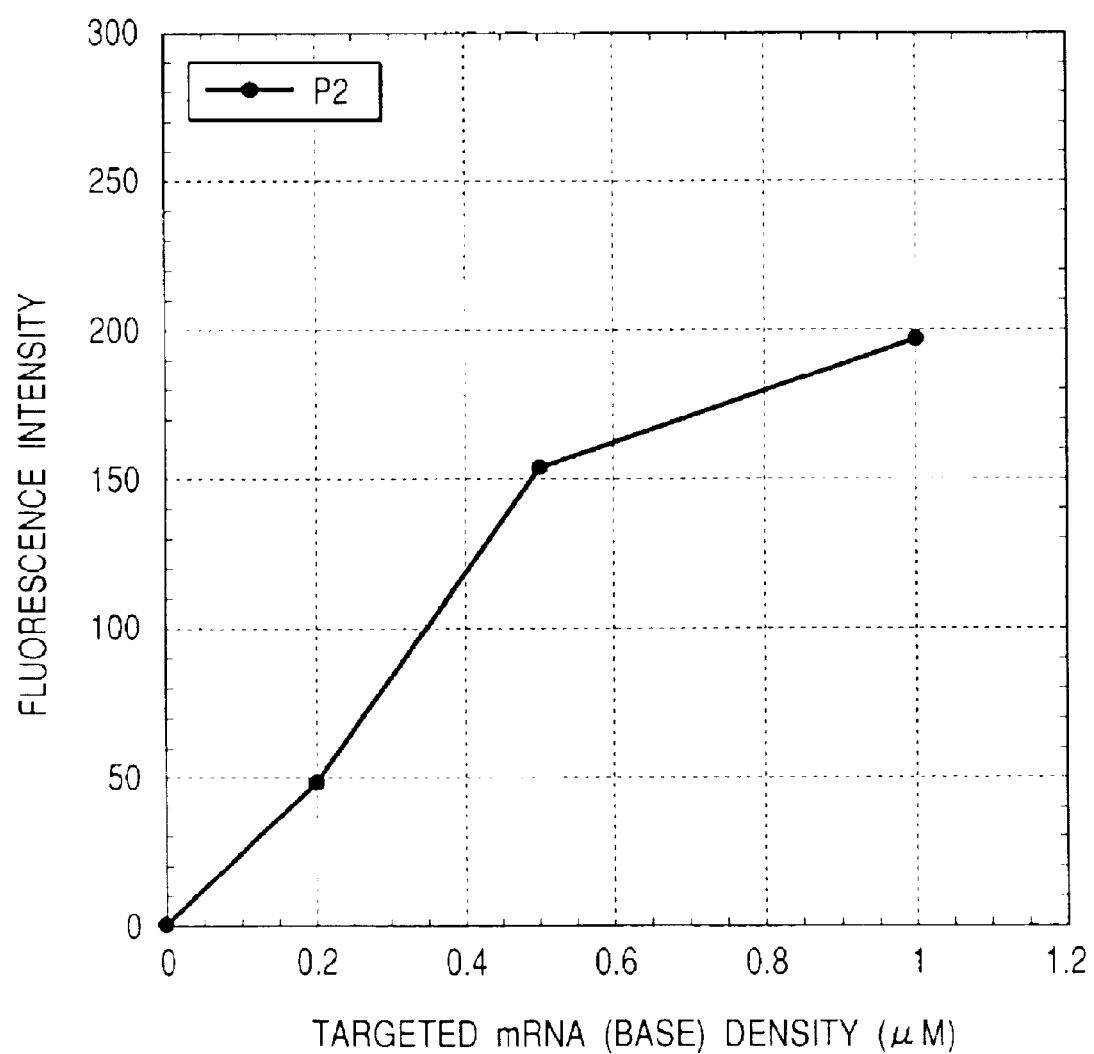
FIG. 8 is a graphical representation of detection/quantification of mRNA using P2 by the probe nucleotide chain fixing method.

The measured results are shown in FIG. 8. It is apparent from FIG. 8 that the targeted mRNA can be detected/quantified by the method of the present invention.

EXAMPLE 7

Detection of Targeted DNA with P2 (targeted nucleotide chain being fixed)

(1) pUC18, which is double-stranded DNA, was obtained (from Takara Shuzo Co., Ltd.) as a targeted nucleotide chain. The targeted base sequence was the same as in Examples 5 and 6, which was on the outside of the restriction enzyme (Hind III) digestion sites at a multiple cloning site. The base sequence was as follows:
5'ACTGGCCGTCGTTTTACAAC3'
(SEQ ID NO: 1)

(2) The above DNA was subjected to complete restriction digestion with EcoR I (from Takara Shuzo Co., Ltd.) by a certain method and recovered by ethanol precipitation.

(3) The recovered DNA was further subjected to complete restriction digestion with Pvu II (from Takara Shuzo Co., Ltd.) and recovered by ethanol precipitation. The recovered DNAs after the restriction enzyme digests contained the following three types of DNAs:

1) double-stranded DNA with blunt ends on both ends of about 2000 base pairs;

2) double-stranded DNA with a blunt end on one end of about 100 base pairs and a sticky end 3'TTAA (AA being on the terminal side) on the other end of the same; and 3) double-stranded DNA with a blunt end on one end of about 200 base pairs and a sticky end 3'TTAA (AA being on the terminal side) on the other end of the same.

The targeted base sequence of (1) exists on the sense strand side having the sticky end.

(4) Two % solution (water:ethanol=1:1) of silane coupling agent with epoxy group (from Shin-Etsu Chemical Co., Ltd., KBM 403, γ-glycidoxypropyltrimethoxysilane) was spin coated on a properly cleaned quartz glass substrate (from Iiyama Special Glass, 25.4×25.4 mm, 0.5 mm thick) and dried at 100° C. for 1 hour. Thus epoxy group was attached on the substrate.

(5) The glass substrate of (4) was reacted with 1 μM DNA solution of (3) (10 mM phosphoric acid buffer solution, pH 7.0, 2 ml) at room temperature for 24 hours. As a result, the amino group of adenine at the pairing end of the double-stranded DNAs of (3)-2) and -3) was reacted with the epoxy group on the substrate and attached thereto.

(6) The above glass substrate was water-washed, heated in 2 mL of water at 95° C. for 10 minutes, and washed with hot water at 95° C. As a result, of the double-stranded DNAs of (3)-2) and -3), each single strand with its pairing end attached on the substrate alone remained on the substrate.

(7) The above substrate was immersed in 2 mL of 1 μM, in terms of the base concentration of the probe nucleotide chain having the same base sequence as those of Examples 4 and 5 (obtained from Kanto Chemical Co., Ltd., with no amino group attached), solution (100 mM Tris-HCl, pH 7.5) so as to be under hybridization conditions and cooled to a final temperature of 4° C. Thus, the probe nucleotide chain formed a hybrid with the DNA attached on the substrate. Each of the following operations before fluorescence detection was carried out at 4° C.

(8) The above glass substrate was washed with 2 mL of the buffer solution of (7) three times and immersed in 2 mL of P2 solution (1 μM) prepared in the same manner as in Example 4 for 10 minutes.

(9) The substrate was washed with 2 mL of the above buffer solution, and the liquid on the substrate was removed with argon gas flow.

(10) The fluorescence intensity was measured in state where the sample was dried up, in the same manner as in Example 4. As a control, measurements were made for the glass substrate which had not been subjected to the attachment operation of (6). The measured results are shown in Table 1.

TABLE 1

| pUC18 Detection Result | | |
|---|---|---|
| | Sample | Blank |
| Fluorescence Intensity | 116 | 2 |

It is apparent from Table 1 that the targeted nucleotide chains attached on the substrate can be detected by the method of the present invention.

COMPARATIVE EXAMPLE 1

Observation of FITC Fluorescence under Dry Conditions

One μM aqueous solution of FITC (from Molecular Probe Co.), to which amino group had been introduced taking into consideration its solubility in water, was prepared, and a proper amount of the same was allowed to penetrate between a slide glass and a cover glass. The fluorescence was observed with a system of a fluorescence microscope (G excitation filter)+ICCD+Argus 50, as in the above example.

As a result, relatively intense fluorescence was observed while water existed between the two glasses, however, no fluorescence was observed in the area where water had been evaporated.

EXAMPLE 8

Detection of Double-stranded Nucleotide Chain with EB, 2-methyl-4,6-bis(4-N,N-dimethylaminophenyl)pyrylium iodide (hereinafter referred to as P2) and YOYO1

(1) One mg of salmon testes DNA (double-stranded DNA, from Sigma Ardrich Japan) was dissolved in 1 mL of 10 mM Tris-HCl buffer solution (pH 7.5) and subjected to ultrasonic breaking properly, so as to obtain DNA with the average length of 200 to 300 base pairs. The DNA length was confirmed by the agarose electrophoresis. This solution was properly diluted with water so as to obtain a 100 μM stock solution in terms of base pair.

(2) Four mg of EB (from Sigma Ardrich Japan) was dissolved in 1 mL of DMSO, and 9 mL of water was added thereto. Additional water was added to the solution to bring about a 100-fold dilution as a 10 μM stock solution.

(3) Five mg of P2 (synthesized by the present inventors) was dissolved in 1 mL of acetonitrile and 9 mL of water was added. Additional water was added to the solution to bring about a 100-fold dilution as a 10 μM stock solution.

(4) Water was added to YOYO1 (from Molecular Probe Co., 1 mM/DMSO) to bring about a 100-fold dilution as a 10 μM stock solution.

(5) Each of 10 μL of dye solutions (final concentration of 1 μM) and each of 0, 2, 5, 10 μL of DNA solutions (final concentrations of 0, 2.0, 5.0 and 10.0 μM, respectively) were mixed, and water was added to 100 μL. Since YOYO1 is unstable when the concentration of salt is low, 10 μL of 100 mM Tms-HCl buffer solution (pH 7.5) were added to a total volume of 100 μL.

(6) 0.5 μL of each solution (5) was placed on a properly cleaned and dried transparent acrylic substrate 1 mm thick (from Asahi Chemical Industry Co., Ltd., Deluglass A). For the solutions in the above state and another solutions having been subjected to the same operation as above and to the drying-up by a vacuum pump, the fluorescence was observed and the intensity of the same was measured. The measurements of fluorescence were promptly carried out in a short time, since the sample might evaporate.

For the fluorescence observation, used was an inverted-type fluorescence microscope IMT2 (objective lens of 10 magnifications) from Olympus Optical Co., Ltd. And as the filter cubes for the fluorescence observation, a G excitation filter was used for each case using EB, a B excitation filter for each case using YOYO1 and a filter specially prepared (by Asahi Bunko, excitation: 580 nm, fluorescence: 540 nm, dichroic mirror: 610 nm) for each case using P2.

For the measurements of fluorescence intensity, used were a CCD equipped with an image intensifier (from Hamamatsu Photonics, ICCD C2400-87) and an image processing apparatus (from Hamamatsu Photonics, Argus 50) which were connected to the above fluorescence microscope via a relay lens (NFK 2.5×LD).

The measurements of fluorescence intensity were carried out in the area of 200×200 μm which was considered to have the average brightness and be uniform to some extent, and the average values on the pixels (2×2 μm) in the area were adopted as measured values. The amplification degree of the image intensifier was 0.2 in terms of the indicated value.

The fluorescence intensity values of the dyes cannot be directly compared because the spectral characteristics of the filters are different from each other, the excitation light source (high pressure mercury lamp) consists of bright lines, and because the sensitivity of the ICCD camera depends on wavelength.

Figure 9:
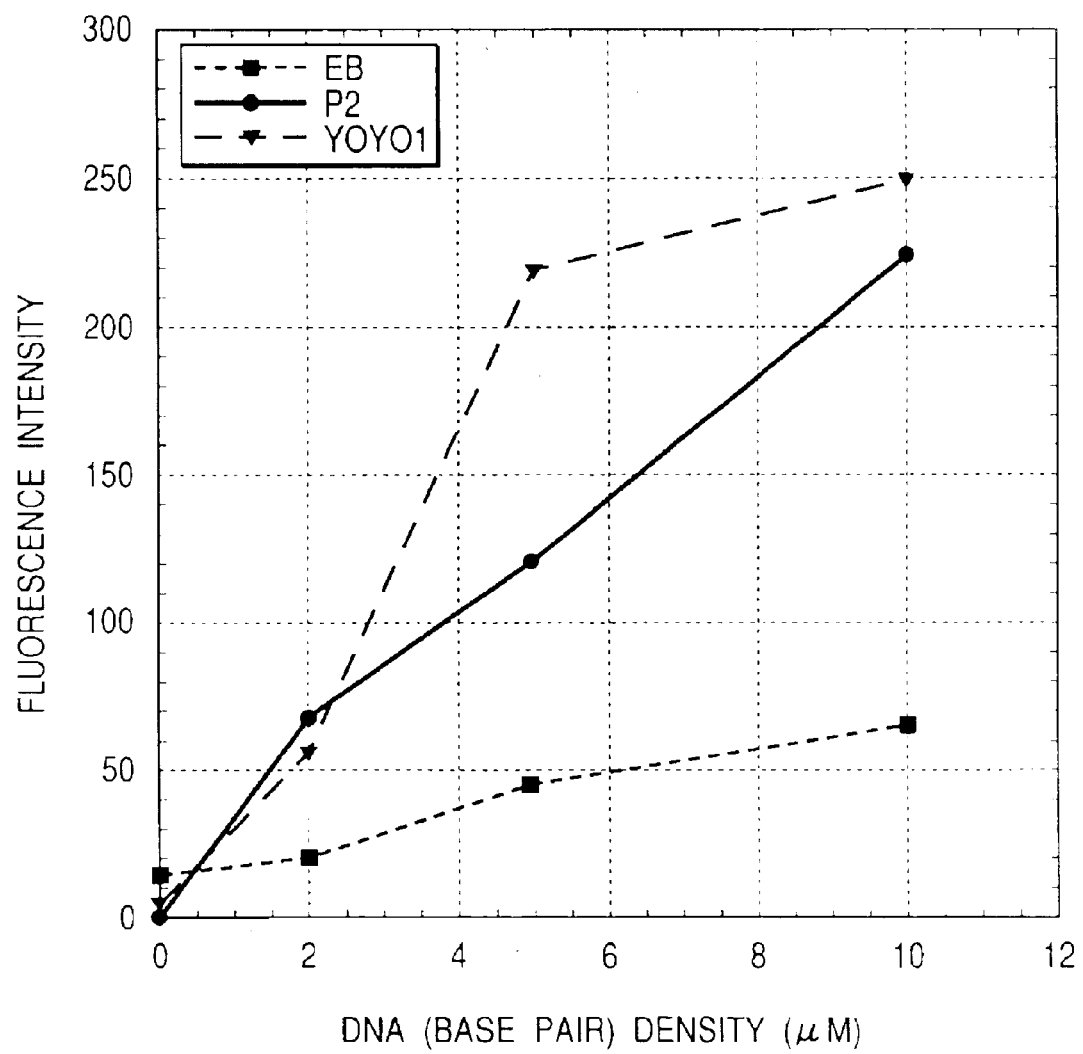
FIG. 9 is a graphical representation of detection/quantification of a double-stranded nucleotide chain using EB, P2 and YOYO1 (solution system)
Figure 10:
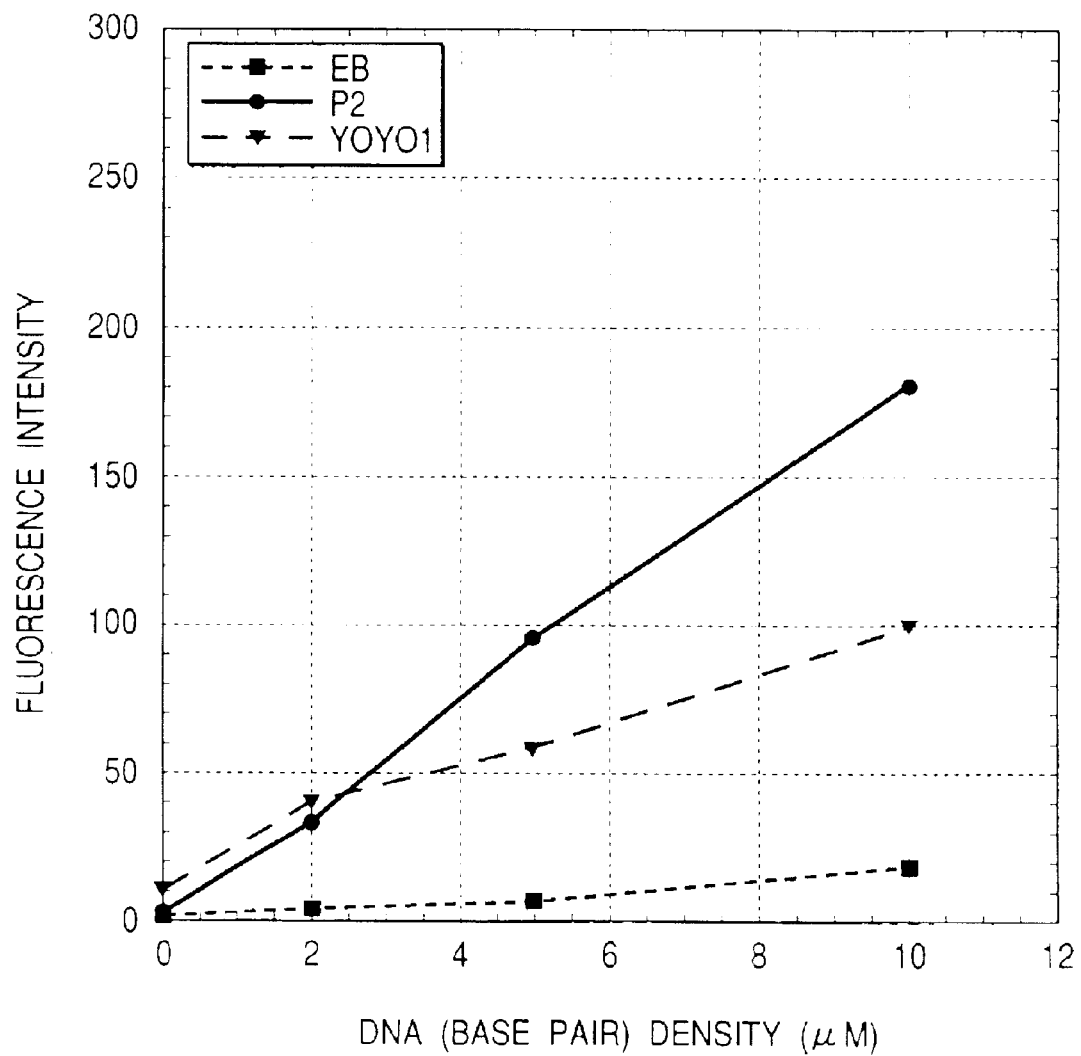
FIG. 10 is a graphical representation of detection/quantification of a double-stranded nucleotide chain using EB, P2 and YOYO1 (dry method)

The measured values of the fluorescence intensity are shown in FIGS. 9 (solution system) and 10 (dry type). It is apparent from FIGS. 9 and 10 that the detection/quantification of double-stranded DNA can be performed even in the dry-up state with any one of EB, P2 and YOYO1, though there are observed differences in fluorescence intensity difference and linearity.

The comparison of the three types of dyes shows that the degree of fluorescence quenching is high in EB and YOYO1, especially in EB, in the dried up state. On the other hand, the degree of fluorescence quenching is relatively low in P2 in the dried up state; accordingly, P2 can be said to be suitable for the measuring method of the present invention.

EXAMPLE 9

Quantification of Triple-stranded Nucleotide Chain with P2

(1) The following 3 types of synthesized 11-mer oligodeoxynucleotides, which form parallel type of triple-stranded chains, were purchased (from Kanto Chemical Co., Ltd.).
a) 5'TTCTTCTTTTC3'
(SEQ ID NO: 5)
b) 3'AAGAAGAAAAG5'
(SEQ ID NO: 6)
c) 3'TTCTTCTTTTC5'
(SEQ ID NO: 7)

Each of 500 μM solutions, in terms of the base pair concentration, of the above oligodeoxynucleotides was annealed in 10 mM phosphoric acid buffer solution (pH 6.5) containing 1M NaCl and 10 mM EDTA (cooled to a final temperature of 4° C.) so as to form a triple-stranded chain and to prepare a 500 μM, in terms of the base trio concentration, (⅓ of the entire base concentration) stock solution. The conditions, such as salt concentration, adopted were considered to be suitable for the formation of triple-stranded chains.

(2) Ten μL of P2 solution used in Example 8 and each of 0, 0.5, 1.0 and 2.0 μL (final concentrations of 0, 2.5, 5.0 and 10.0 μM) of DNA solutions of (1) were mixed, and water was added to each solution to a final volume of 100 μL.

(3) The fluorescence intensity was measured in state where the sample was dried up, in the same manner as in Example 8.

The measured results are shown in FIG. 11. In order to make possible the comparison with the results of Example 1, the amplification degree of the image intensifier and the ordinate of the graph were the same as those of Example 1. It is apparent from FIG. 11 that triple-stranded nucleotide chains can be detected/quantified by the method of the present invention.

EXAMPLE 10

Quantification of Quadruple-stranded Nucleotide Chain with P2

(1) The following synthesized oligodeoxynucleotide, which has human telomere sequence contributing to the formation of quadruple-stranded chains, was purchased (from Kanto Chemical Co., Ltd.).
d(TTGGG)$_2$ 400 μM solution of the above oligodeoxynucleotide was annealed in 20 mM Tris-HCl buffer solution (pH 7.2) containing 10 mM K+ (cooled to a final temperature of 4° C.) so as to form a quadruple-stranded chain and to prepare a 100 μM, in terms of the base quartet concentration, (¼ of the entire base concentration) stock solution.

(2) Ten μL of P2 solution used in Example 8 and each of 0, 2, 5 and 10 μL (final concentrations of 0, 2.0, 5.0 and 10.0 μM) of DNA solutions of (1) were mixed, and water was added to each solution to a final volume of 100 μL.

(3) The fluorescence intensity was measured in state where the sample was dried up, in the same manner as in Example 9.

The measured results are shown in FIG. 12. In order to make possible the comparison with the results of Examples 8 and 9, the amplification degree of the image intensifier and the ordinate of the graph were the same as those of Examples 8 and 9. It is apparent from FIG. 12 that quadruple-stranded nucleotide chains can be detected/quantified by the method of the present invention.

COMPARATIVE EXAMPLE 2

Observation of FITC Fluorescence under Dry Conditions

One $\mu$M aqueous solution of FITC (from Molecular Probe Co.), to which amino group had been introduced taking into consideration its solubility in water, was prepared, and a proper amount of the same was allowed to penetrate between a slide glass and a cover glass. The fluorescence was observed with a system of a fluorescence microscope (G excitation filter)+ICCD+Argus 50, as in the above examples.

As a result, relatively intense fluorescence was observed while water existed between the two glasses, however, no fluorescence was observed in the area where water had been evaporated.

What is claimed is:

1. A method for dry detection/quantification of targeted nucleotide chains, comprising the steps of:
   (1) forming a hybrid (C) of a certain amount of a targeted nucleotide chain (A), and a probe nucleotide chain (B), which has a base sequence complementary to a specific site of the base sequence of said targeted nucleotide chain, on a solid-phase substrate by mutually reacting the two types of nucleotide chains with each other, and in which there exists a fluorescence dye (D), which acts on said hybrid (C), thereby emits fluorescence or increases its fluorescence intensity, and is capable of continuing to emit fluorescence even in a dried state while acting on said hybrid;
   (2) drying said hybrid (C) and said fluorescence dye (D) on said substrate; and
   (3) measuring the fluorescence emitted from said fluorescence dye (D), as measuring means, after the drying operation.

2. The method according to claim 1, wherein, in said step (1), both of the formation (1-1) of said hybrid (C) and the action (1-2) of said fluorescence dye (D) on said hybrid (C) are carried out in state where they are dissolved in a sample solution.

3. The method according to claim 1, wherein, in said step (1), both of the formation (1-1) of said hybrid (C) and the action (1-2) of said fluorescence dye (D) on said hybrid (C) are carried out in state where they are fixed on said substrate.

4. The method according to claim 3, further comprising a step (1-0) of fixing said probe nucleotide chain (B) on the surface of said substrate before allowing said probe nucleotide chain (B) to act on said targeted nucleotide chain (A).

5. The method according to claim 3, further comprising a step (1-0') of fixing said targeted nucleotide chain (A) on the surface of said substrate before allowing said targeted nucleotide chain (A) to act on said probe nucleotide chain (B).

6. The method according to claim 3, further comprising a step (1-1') of removing the nucleotide chain other than said hybrid (C) in a solution by washing operation after the formation (1-1) of said hybrid (C) and before the action (1-2) of said fluorescence dye (D) on said hybrid (C) in said step (1).

7. The method according to claim 3, further comprising a step (1-3) of removing said fluorescence dye (D) not having acted on said hybrid (C) by washing operation after the action (1-2) of said fluorescence dye (D) on said hybrid (C) in said step (1).

8. The method according to claim 3, further comprising a step (1-4) of removing a solvent from said hybrid (C) and said fluorescence dye (D) having acted on said hybrid (C) by gas flow between said steps (1) and (2).

9. The method according to claim 1, wherein said solid-phase substrate is a glass substrate.

10. The method according to claim 1, wherein said solid-phase substrate is a resin substrate.

11. The method according to claim 1, wherein said targeted nucleotide chain (A) is a single-stranded nucleotide chain.

12. The method according to claim 1, wherein said targeted nucleotide chain (A) is DNA.

13. The method according to claim 1, wherein said targeted nucleotide chain (A) is RNA.

14. The method according to claim 13, wherein said targeted nucleotide chain (A) is mRNA.

15. The method according to claim 1, wherein said fluorescence dye (D) is an intercalator which enters the space between the two base pairs of a double-stranded nucleotide chain.

16. The method according to claim 1, wherein said fluorescence dye (D) is a groove binding type dye which enters the groove of a double-stranded nucleotide chain.

17. The method according to claim 15, wherein said fluorescence dye (D) is 2-methyl-4,6-bis(4-N,N-dimethylaminophenyl)pyrylium salt.

18. The method according to claim 15, wherein said fluorescence dye (D) is ethidium bromide.

19. The method according to claim 16, wherein said fluorescence dye (D) is YOYO1.

20. A method for dry detection/quantification of multi-stranded nucleotide chains, comprising the steps of:

(1) adding to a sample solution, which is subjected to detection/quantification of a multi-stranded nucleotide chain, a fluorescence dye having a fluorescence characteristic of emitting fluorescence or increasing its fluorescence intensity in the presence of a multi-stranded nucleotide chain and capable of maintaining the fluorescence characteristic in a dried state;

(2) placing a known amount of said sample solution with said fluorescence dye added thereto on a clean substrate so as to dry the sample solution; and (3) measuring the fluorescence emitted from the dried sample and detecting/quantifying said multi-stranded nucleotide chain in said sample solution based on obtained measured values.

21. The method according to claim 20, wherein said multi-stranded nucleotide chain is any one of double-stranded nucleotide chain, triple-stranded nucleotide chain and quadruple-stranded nucleotide chain.

22. The method according to claim 20, wherein said fluorescence dye is an intercalator which enters the space between the two base pairs of a doublestranded nucleotide chain.

23. The method according to claim 20, wherein said fluorescence dye is a groove binding type dye which enters the groove of a double-stranded nucleotide chain.

24. The method according to claim 22, wherein said fluorescence dye is 2-methyl-4,6-bis(4-N,N-dimethylaminophenyl)pyrylium salt.

25. The method according to claim 22, wherein said fluorescence dye is ethidium bromide.

26. The method according to claim 23, wherein said fluorescence dye is YOYO1.

* * * * *

UNITED STATES PATENT AND TRADEMARK OFFICE
CERTIFICATE OF CORRECTION

PATENT NO.         : 6,960,432 B2
APPLICATION NO. : 09/764050
DATED                  : November 1, 2005
INVENTOR(S)       : Tadashi Okamoto et al.

It is certified that error appears in the above-identified patent and that said Letters Patent is hereby corrected as shown below:

On Title Page Item (56) col. 1
References Cited, Foreign Patent Documents, "03095862" should read --03-095862--.

IN THE DRAWINGS
FIG. 8, "TERGETED" should read --TARGETED--.

COLUMN 1
Line 46, "72th" should read --72nd--; and
Line 51, "of the" should read --the--.

COLUMN 7
Line 1, "types" should read --types of--.

COLUMN 10
Line 54, "another" should read --other--.

COLUMN 13
Line 7, "NO. 2)" should read --NO: 2)--; and
Line 24, "the solution" should read --the solutions--.

COLUMN 14
Line 21, "NO. 2)" should read --NO: 2)--; and
Line 42, "in state" should read --in a state where--.

COLUMN 15
Line 1, "-$NH_2$5" should read -- -$NH_2$5'--; and
Line 23, "in state" should read --in a state where--.

COLUMN 17
Line 26, "another" should read --other--.

UNITED STATES PATENT AND TRADEMARK OFFICE
CERTIFICATE OF CORRECTION

PATENT NO. : 6,960,432 B2
APPLICATION NO. : 09/764050
DATED : November 1, 2005
INVENTOR(S) : Tadashi Okamoto et al.

It is certified that error appears in the above-identified patent and that said Letters Patent is hereby corrected as shown below:

COLUMN 24
Line 3, "doublestranded" should read --double-stranded--.

Signed and Sealed this

Twenty-fourth Day of October, 2006

JON W. DUDAS
*Director of the United States Patent and Trademark Office*

SEQUENCE LISTING

```
<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:Synthesized

<400> SEQUENCE: 1
actggccgtc gtttatcaac                                                 20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:Synthesized

<400> SEQUENCE: 2
gttgtaaaac gacggccagt                                                 20

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence:Synthesized

<400> SEQUENCE: 3
tgctgtgcgt cacggccagc at                                              22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence:Synthesized

<400> SEQUENCE: 4
atgctggccg tgacgcacag ca                                              22

<210> SEQ ID NO 5
<211> LENGTH: 11
<212> TYPE: DNA
<213> ORGANISM: Artificial Sequence
<220> FEATURE:
<223> OTHER INFORMATION: Description of Artificial Sequence:Synthesized DNA single chain pr
      epared for a triple chain.

<400> SEQUENCE: 5
ttcttctttt c                                                          11
```

```
                              -continued

<210> SEQ ID NO 6
<211> LENGTH: 11
<212> TYPE: DNA
<213> ORGANISM: Artificial Sequence
<220> FEATURE:
<223> OTHER INFORMATION: Description of Artificial Sequence:Synthesized DNA single chain pr
      epared for a triple chain.

<400> SEQUENCE: 6
gaaaagaaga a                                                                            11

<210> SEQ ID NO 7
<211> LENGTH: 11
<212> TYPE: DNA
<213> ORGANISM: Artificial Sequence
<220> FEATURE:
<223> OTHER INFORMATION: Description of Artificial Sequence:Synthesized DNA single chain pr
      epared for a triple chain.

<400> SEQUENCE: 7
cttttcttct t                                                                            11
```